(12) United States Patent
Yamamoto et al.

(10) Patent No.: US 10,265,220 B2
(45) Date of Patent: Apr. 23, 2019

(54) MANUFACTURING APPARATUS AND MANUFACTURING METHOD FOR MANUFACTURING COMPOSITE SHEET ASSOCIATED WITH ABSORBENT ARTICLE

(71) Applicant: Unicharm Corporation, Ehime (JP)

(72) Inventors: Hiroki Yamamoto, Kagawa (JP);
Yoshihiko Matsumoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 101 days.

(21) Appl. No.: 15/128,548

(22) PCT Filed: Oct. 16, 2014

(86) PCT No.: PCT/JP2014/077492
§ 371 (c)(1),
(2) Date: Sep. 23, 2016

(87) PCT Pub. No.: WO2015/145837
PCT Pub. Date: Oct. 1, 2015

(65) Prior Publication Data
US 2017/0128277 A1  May 11, 2017

(30) Foreign Application Priority Data

Mar. 27, 2014  (JP) .................................. 2014-065247

(51) Int. Cl.
*A61F 13/15* (2006.01)
*G05B 19/18* (2006.01)

(52) U.S. Cl.
CPC .. *A61F 13/15772* (2013.01); *A61F 13/15585* (2013.01); *A61F 13/15707* (2013.01);
(Continued)

(58) Field of Classification Search
CPC .......... A61F 13/15772; A61F 13/15707; A61F 13/15796; A61F 13/15715; A61F 13/15699; A61F 13/15747
See application file for complete search history.

(56) References Cited

U.S. PATENT DOCUMENTS

| 2004/0007318 A1* | 1/2004 | Popp ................ A61F 13/15577 |
| | | 156/256 |
| 2012/0090071 A1 | 4/2012 | Umebayashi |
| 2013/0175312 A1 | 7/2013 | Nakano |

FOREIGN PATENT DOCUMENTS

| EP | 2 135 590 A1 | 12/2009 |
| JP | 2007-105453 A | 4/2007 |

(Continued)

OTHER PUBLICATIONS

International Search Report from corresponding PCT application No. PCT/JP2014/077492 dated Jan. 6, 2015 (4 pgs).
(Continued)

*Primary Examiner* — Mark A Osele
*Assistant Examiner* — Christopher C Caillouet
(74) *Attorney, Agent, or Firm* — Brinks Gilson & Lione

(57) ABSTRACT

A manufacturing apparatus for manufacturing a composite sheet associated with an absorbent article, including: a producing device that produces a substrate sheet by fixing a stretchable sheet to at least low-extensible sheet, the stretchable sheet continuing along a transporting direction, the stretchable sheet being in an extended state in which the stretchable sheet is extended in the transporting direction, the producing is performed while the producing device is transporting the stretchable sheet; a reference-section forming apparatus that forms a physical reference section on the substrate sheet, the substrate sheet being in a first extended state and being transported; a contraction apparatus in which the substrate sheet that has the reference section formed on
(Continued)

it contracts until the substrate sheet becomes in a second extended state whose extension ratio is smaller than an extension ratio of the first extended state; and a processing apparatus that performs the certain process to the substrate sheet, the substrate sheet having contracted and being in the second extended state. The contraction apparatus includes: a transport path in which the substrate sheet is transported; a sensor that detects the reference section after the contraction in the contraction apparatus and that outputs a detection signal; and an alteration device that alters a transportation state of the substrate sheet in the transport path so that a position in the substrate sheet for the certain process is located close to a target position for the certain process, the alteration being performed according to the detection signal of the sensor.

20 Claims, 8 Drawing Sheets

(52) U.S. Cl.
CPC .. *G05B 19/182* (2013.01); *A61F 2013/15715* (2013.01); *A61F 2013/15796* (2013.01); *A61F 2013/15869* (2013.01); *A61F 2013/15878* (2013.01); *A61F 2013/15918* (2013.01); *G05B 2219/35188* (2013.01)

(56) References Cited

FOREIGN PATENT DOCUMENTS

| | | |
|---|---|---|
| JP | 2008-143699 A | 6/2008 |
| JP | 2009-132473 A | 6/2009 |
| JP | 2010-284430 A | 12/2010 |
| JP | 2012-050883 A | 3/2012 |
| JP | 2013-248146 A | 12/2013 |
| WO | WO 98/21035 | 5/1998 |
| WO | WO 2013/166095 A1 | 11/2013 |

OTHER PUBLICATIONS

European communication from corresponding European application No. 14887564.4 dated Dec. 14, 2017 (4 pgs).

European extended Search Report from corresponding European application No. 14887564.4 dated Apr. 26, 2017 (6 pgs).

International Preliminary Report on Patentability and Written Opinion from corresponding PCT application No. PCT/JP2014/077492 dated Sep. 27, 2016 (7 pgs).

* cited by examiner

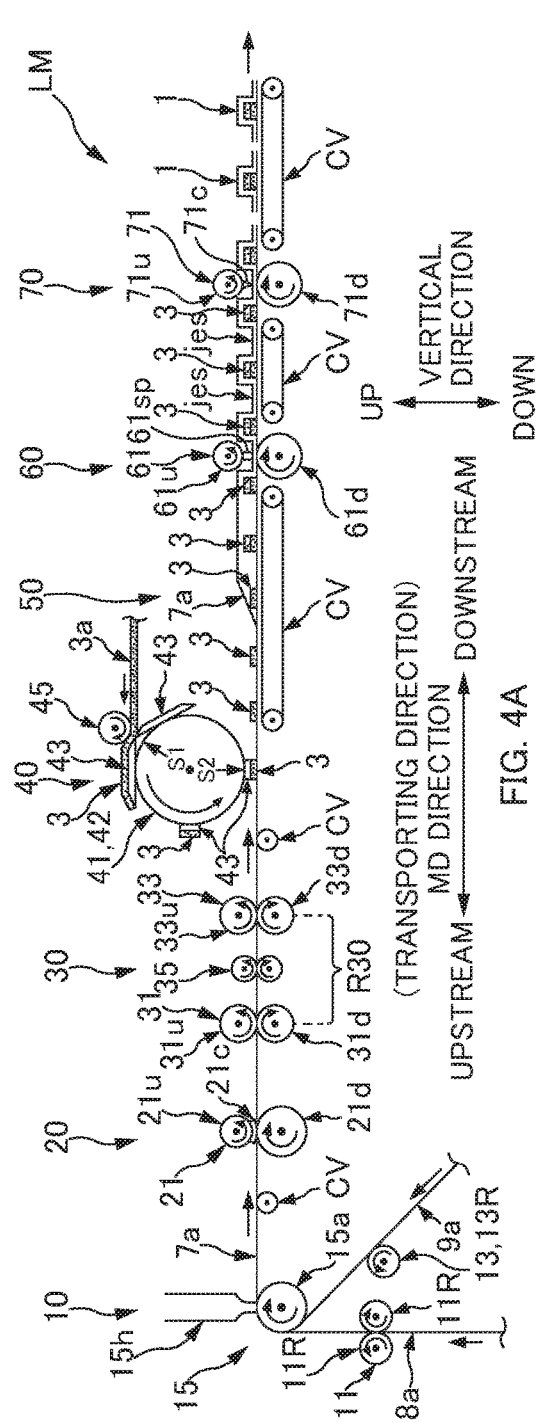
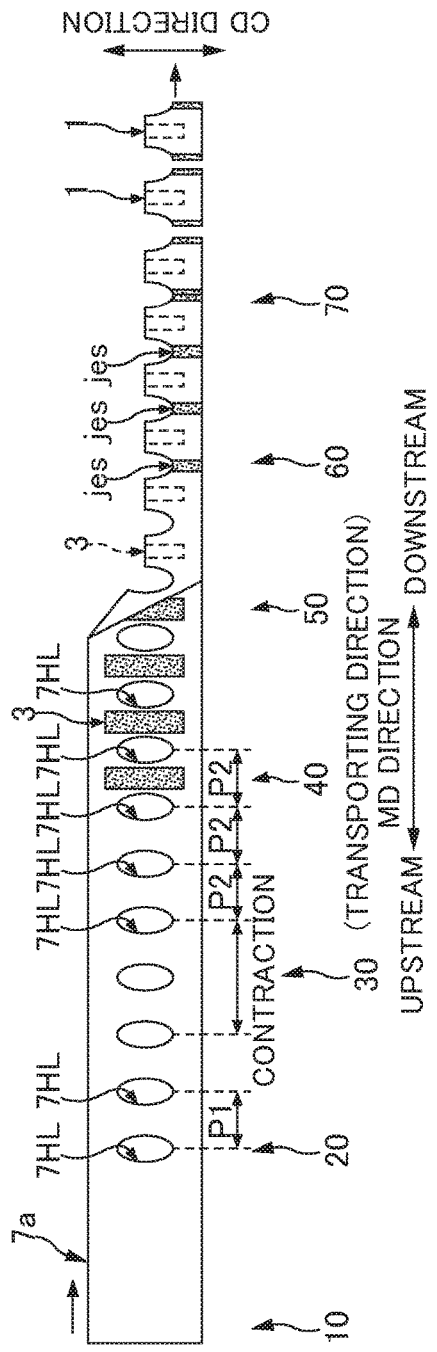
FIG. 4A
FIG. 4B

VIEW ALONG LINE B-B

MANUFACTURING APPARATUS AND MANUFACTURING METHOD FOR MANUFACTURING COMPOSITE SHEET ASSOCIATED WITH ABSORBENT ARTICLE

RELATED APPLICATION

The present application is a 35 U.S.C. § 371 national stage filing of International Patent Application No. PCT/JP2014/077492, filed Oct. 16, 2014, to which priority is claimed under 35 U.S.C. § 120 and through which priority is claimed under 35 U.S.C. § 119 to Japanese Priority Patent Application No. 2014-065247, filed Mar. 27, 2014, the entire disclosure of which is hereby incorporated by reference.

TECHNICAL FIELD

The invention relates to a manufacturing apparatus and a manufacturing method for manufacturing a composite sheet associated with an absorbent article such as a disposable diaper.

BACKGROUND ART

In a manufacturing line of a disposable diaper which is an example of an absorbent article, a stretchable sheet is in an extended state of a certain extension ratio and is transported in a transporting direction, and a substrate sheet is produced by stacking and joining the stretchable sheet onto a low-extensible sheet. In the general case, the substrate sheet remains in the foregoing extended state and is being transported to the downstream process. In the downstream process, the substrate sheet being in the foregoing extended state sequentially undergoes suitable processes such as attaching an absorbent main body which absorbs liquid. Then, the substrate sheet is divided into unit parts each of which corresponds to a single finished diaper. Finally, the diaper is produced.

Following the dividing, the extension of the substrate sheet is released and the substrate sheet contracts in the transporting direction. The substrate sheet is used in the exterior of a diaper, and a plurality of creases are generated in the exterior along a direction intersecting the transporting direction. Accordingly, a finished diaper is at least in a state which the diaper has contracted and is able to extend till the creases completely stretch. As a result, a diaper user such as a wearer can use a stretchable diaper.

CITATION LIST

Patent Literature

[Patent Literature 1] Japanese Unexamined Patent Application Publication No. 2007-105453

SUMMARY OF INVENTION

Technical Problem

In some cases, the foregoing processes is effectively perform after the extended state of the substrate sheet is released in a certain degree, that is, after the substrate sheet becomes in a second extended state whose extension ratio is smaller than the extension ratio of the foregoing extended state. An example thereof will be described below.

If an absorbent main body is attached to the substrate sheet which is in the extended state, when the extended state is released, creases are generated in the absorbent main body due to contraction force which is applied to the absorbent main body from the substrate sheet. This may cause deterioration of liquid absorbency of the absorbent main body because of area reduction of the surface facing wearer's skin, and may also cause leakage of urine through the creases. In this regard, before attaching the absorbent main body, if the extended state of the substrate sheet is released (e.g. by 10% of the extension ratio) as mentioned above, the contraction force which is applied to the absorbent main body from the substrate sheet is reduced by the amount of the contraction of the substrate sheet caused by the release. This allows the absorbent main body to be substantially flat and less creased. This makes it possible to enlarge the area of the surface facing wearer's skin. And, this can prevent a trouble such as deterioration of liquid absorbency of the absorbent main body, which is caused by contraction of the absorbent main body.

However, the magnitude of contraction deformation of the substrate sheet could vary depending on each part of the same sheet. This makes it difficult to perform the foregoing various processes (e.g. attaching the absorbent main body after 10% contraction) at target positions in the substrate sheet.

The invention has been made in view of the above problems, and an advantage thereof is to achieve a processing of a substrate sheet at an exact target position even if the substrate sheet has contracted from the first extended state to the second extended state.

Solution to Problem

An aspect of the invention to achieve the above advantage is a manufacturing apparatus for manufacturing a composite sheet associated with an absorbent article, the manufacturing being performed by producing a substrate sheet and performing a certain process to the substrate sheet, the substrate sheet including a stretchable sheet and a low-extensible sheet, the low-extensible sheet having an extensibility lower than that of the stretchable sheet, the manufacturing apparatus including:

a producing device that produces the substrate sheet by fixing the stretchable sheet to at least the low-extensible sheet, the stretchable sheet continuing along a transporting direction the stretchable sheet being in an extended state in which the stretchable sheet is extended in the transporting direction, the producing is performed while the producing device is transporting the stretchable sheet;

a reference-section forming apparatus that forms a physical reference section on the substrate sheet, the substrate sheet being in a first extended state and being transported;

a contraction apparatus in which the substrate sheet that has the reference section formed on it contracts until the substrate sheet becomes in a second extended state whose extension ratio is smaller than an extension ratio of the first extended state; and a processing apparatus that performs the certain process to the substrate sheet, the substrate sheet having contracted and being in the second extended state, the contraction apparatus including:
a transport path in which the substrate sheet is transported;
a sensor
that detects the reference section after the contraction in the contraction apparatus and
that outputs a detection signal; and
an alteration device that alters a transportation state of the substrate sheet in the transport path so that a position in the substrate sheet for the certain process is located close to a target position for the certain process,
the alteration being performed according to the detection signal of the sensor.
Further,
a manufacturing method for manufacturing a composite sheet associated with an absorbent article,
the manufacturing being performed by producing a substrate sheet and performing a certain process to the substrate sheet,
the substrate sheet including a stretchable sheet and a low-extensible sheet,
the low-extensible sheet having an extensibility lower than that of the stretchable sheet,
the manufacturing method including:
producing the substrate sheet by fixing the stretchable sheet to at least the low-extensible sheet,
the stretchable sheet continuing along a transporting direction,
the stretchable sheet being transported,
the stretchable sheet being in an extended state in which the stretchable sheet is extended in the transporting direction;
forming a physical reference section on the substrate sheet,
the substrate sheet being in a first extended state and being transported;
causing the substrate sheet to contract in a contraction apparatus until the substrate sheet becomes in a second extended state whose extension ratio is smaller than an extension ratio of the first extended state,
the substrate sheet having the reference section formed on it; and
performing the certain process by a processing apparatus to the substrate sheet,
the substrate sheet having contracted and being in the second extended state,
causing the substrate sheet to contract including:
transporting the substrate sheet in a transport path;
detecting the reference section by a sensor and outputting a detection signal by a sensor after the contraction in the contraction apparatus; and
altering a transportation state of the substrate sheet in the transport path so that a position in the substrate sheet for the certain process by the processing apparatus is located close to a target position for the certain process,
the altering being performed according to the detection signal of the sensor.
Other features of this invention will become apparent from the description in this specification and the attached drawings.

Advantageous Effects of Invention

According to the invention, it is possible to achieve a processing of a substrate sheet at an exact target position even if the substrate sheet has contracted from the first extended state to the second extended state.

BRIEF DESCRIPTION OF DRAWINGS

FIG. 4A is a schematic side view of a manufacturing line LM which manufactures the diaper 1,
and FIG. 4B is a schematic plan view showing how diapers 1 are manufactured.

DESCRIPTION OF EMBODIMENTS

Figure 1:
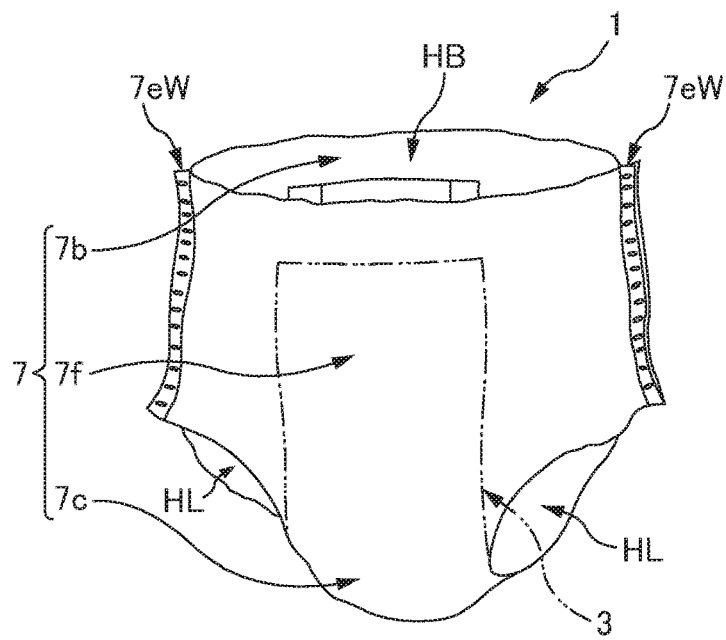
FIG. 1 is a schematic perspective view of a pull-on diaper 1 exemplifying an absorbent article according to the present embodiment.

At least the following matters will be made clear by the description in the present specification and the accompanying drawings.
A manufacturing apparatus for manufacturing a composite sheet associated with an absorbent article,
the manufacturing being performed by producing a substrate sheet and performing a certain process to the substrate sheet,
the substrate sheet including a stretchable sheet and a low-extensible sheet,
the low-extensible sheet having an extensibility lower than that of the stretchable sheet,
the manufacturing apparatus including:
a producing device that produces the substrate sheet by fixing the stretchable sheet to at least the low-extensible sheet,
the stretchable sheet continuing along a transporting direction
the stretchable sheet being in an extended state in which the stretchable sheet is extended in the transporting direction,
the producing is performed while the producing device is transporting the stretchable sheet;
a reference-section forming apparatus that forms a physical reference section on the substrate sheet,
the substrate sheet being in a first extended state and being transported;
a contraction apparatus in which the substrate sheet that has the reference section formed on it contracts until the substrate sheet becomes in a second extended state whose extension ratio is smaller than an extension ratio of the first extended state; and a processing apparatus that performs the certain process to the substrate sheet, the substrate sheet having contracted and being in the second extended state, the contraction apparatus including:

a transport path in which the substrate sheet is transported;

a sensor that detects the reference section after the contraction in the contraction apparatus and that outputs a detection signal; and an alteration device that alters a transportation state of the substrate sheet in the transport path so that a position in the substrate sheet for the certain process is located close to a target position for the certain process, the alteration being performed according to the detection signal of the sensor.

With such a manufacturing apparatus for manufacturing a composite sheet associated with an absorbent article, when the substrate sheet is in the first extended state in which the extension ratio is large, the reference section is formed on the substrate sheet. This makes it possible to form the reference section substantially without being affected by fluctuation of the contraction. Consequently, the reference section can be formed exactly at its target position in the substrate sheet. Thus, the reference section can effectively function as a positional reference on a substrate sheet.

The sensor detects the reference section after the contraction in the contraction apparatus, and outputs the detection signal. According to the detection signal, alteration device alters the transportation state of the substrate sheet in the transport path of the contraction apparatus. Thus, the position in the substrate sheet for the certain process is adjusted so as to be located close to its target position. Consequently, concerning the substrate sheet which has contracted in the contraction apparatus till the second extended state, the processing apparatus can perform a process exactly at its target position on the substrate sheet.

In such a manufacturing apparatus for manufacturing a composite sheet associated with an absorbent article, it is desirable that when the transport path is divided into an upstream path section and a downstream path section, the downstream path section being located downstream in the transporting direction from the upstream path section, the alteration device is arranged at a boundary position between the upstream path section and the downstream path section.

With such a manufacturing apparatus for manufacturing a composite sheet associated with an absorbent article, when the transport path included in the foregoing contraction apparatus is divided into the upstream path section and the downstream path section, the alteration device is arranged at a boundary position between these two path sections. With high responsivity, the transportation state of the substrate sheet which is moving in the transport path can be therefore altered according to the detection signal.

In such a manufacturing apparatus for manufacturing a composite sheet associated with an absorbent article, it is desirable that the alteration device includes a roll whose outer circumferential surface comes into contact with the substrate sheet and that is driven and rotated, and the transportation state of the substrate sheet in the transport path is altered by altering a circumferential speed value of the roll.

With such a manufacturing apparatus for manufacturing a composite sheet associated with an absorbent article, the transportation state of the substrate sheet in the transport path is altered by altering a circumferential speed value of the roll. This makes it possible to quickly and securely alter the transportation state.

In such a manufacturing apparatus for manufacturing a composite sheet associated with an absorbent article, it is desirable that the alteration device includes a controller that controls the roll according to the detection signal, when the detection signal indicates that a target position in a substrate sheet for the certain process is shifted upstream in the transporting direction from a position at which the certain process has been performed by the processing apparatus, the controller increases the circumferential speed value of the roll, and when the detection signal indicates that the target position in the substrate sheet for the certain process is shifted downstream in the transporting direction from a position at which the certain process has been performed by the processing apparatus, the controller decreases the circumferential speed value of the roll.

With such a manufacturing apparatus for manufacturing a composite sheet associated with an absorbent article, the controller increases and decreases the circumferential speed value of the roll according to the detection signal as mentioned above. Accordingly, the position in the substrate sheet for the certain process can be securely adjusted so as to be located closer to the target position for the certain process.

In such a manufacturing apparatus for manufacturing a composite sheet associated with an absorbent article, it is desirable that the alteration device includes a roll whose outer circumferential surface comes into contact with the substrate sheet and that is capable of rotating, the transportation state of the substrate sheet in the transport path is altered by reciprocating motion of the roll along a thickness direction of the substrate sheet.

With such a manufacturing apparatus for manufacturing a composite sheet associated with an absorbent article, the transportation state of the substrate sheet in the transport path is altered by reciprocating motion of the roll along a thickness direction of the substrate sheet. This makes it possible to quickly and securely alter the transportation state.

In such a manufacturing apparatus for manufacturing a composite sheet associated with an absorbent article, it is desirable that the alteration device includes a controller that controls the roll according to the detection signal, when the detection signal indicates that a target position in a substrate sheet for the certain process is shifted upstream in the transporting direction from a position at which the certain process has been performed by the processing apparatus, the controller moves the roll in the thickness direction so that a loop of the substrate sheet formed by the roll becomes smaller, and when the detection signal indicates that the target position in the substrate sheet for the certain process is shifted downstream in the transporting direction from a position at which the certain process has been performed by the processing apparatus, the controller moves the roll in the thickness direction so that a loop of the substrate sheet formed by the roll becomes larger.

With such a manufacturing apparatus for manufacturing a composite sheet associated with an absorbent article, the controller adjusts the size of the loop of the substrate sheet formed by the roll, and the adjustment is performed according to the detection signal as mentioned above. Accordingly, the position in the substrate sheet for the certain process can be securely adjusted so as to be located closer to target position for the certain process.

In such a manufacturing apparatus for manufacturing a composite sheet associated with an absorbent article, it is desirable that on the substrate sheet which is in the first extended state, parts each of which is to be the absorbent article are aligned in the transporting direction at a first pitch, and the reference-section forming apparatus forms a leg opening of the absorbent article on the substrate sheet, the leg opening being aligned at the first pitch and serving as the reference section.

With such a manufacturing apparatus for manufacturing a composite sheet associated with an absorbent article, the leg opening is used as the reference section. Accordingly, other processes necessary to manufacture the absorbent article can be performed using the leg opening as a reference. This makes it possible to manufacture an absorbent article with which a wearer is less likely to feel uncomfortable.

In such a manufacturing apparatus for manufacturing a composite sheet associated with an absorbent article, it is desirable that the reference-section forming apparatus prints a mark on the substrate sheet as the reference section.

With such a manufacturing apparatus for manufacturing a composite sheet associated with an absorbent article, the mark is printed as the reference section. This makes it possible to easily form the reference section on the substrate sheet.

In such a manufacturing apparatus for manufacturing a composite sheet associated with an absorbent article, it is desirable that the reference-section forming apparatus prints the mark on the low-extensible sheet of the substrate sheet.

With such a manufacturing apparatus for manufacturing a composite sheet associated with an absorbent article, the mark is printed as the reference section on the low-extensible sheet of the substrate sheet. Accordingly, because of low extensibility of the low-extensible sheet, the mark can serve as more precise reference section.

In such a manufacturing apparatus for manufacturing a composite sheet associated with an absorbent article, it is desirable that on the substrate sheet which is in the first extended state, parts each of which is to be the absorbent article are aligned in the transporting direction at a first pitch, and when a pitch obtained by reducing the first pitch at a ratio of the extension ratio in the second extended state to the extension ratio of the first extended state is defined as a second pitch, the processing apparatus performs the certain process to the substrate sheet at the second pitch.

With such a manufacturing apparatus for manufacturing a composite sheet associated with an absorbent article, the substrate sheet which is in the second extended state is subject to the certain process at the foregoing second pitch. This makes it possible to securely perform the certain process for each part of the substrate sheet, the part is a part that is to be the absorbent article.

In such a manufacturing apparatus for manufacturing a composite sheet associated with an absorbent article, it is desirable that the absorbent article includes an absorbent main body that absorbs liquid, and the processing apparatus attaches the absorbent main body to the substrate sheet at the second pitch, the attachment being performed as the certain process.

With such a manufacturing apparatus for manufacturing a composite sheet associated with an absorbent article, the absorbent main body is attached to the substrate sheet, the attachment being performed as the certain process. Accordingly, the absorbent main body can be attached to the substrate sheet precisely.

The extended state of the substrate sheet at the time of attachment of the absorbent main body is the second extended state in which the substrate sheet has contracted from the first extended state. Accordingly, in the absorbent article whose extended state has been finally released, the amount of creases which are produced on the absorbent main body is reduced by an amount corresponding to the contraction.

In such a manufacturing apparatus for manufacturing a composite sheet associated with an absorbent article, it is desirable that concerning the substrate sheet that is in the second extended state and that is in a two-folded state in which the substrate sheet is two-folded in a width direction of the substrate sheet, in the processing apparatus, the substrate sheet is fixed in the two-folded state by forming a joined part on the substrate sheet at the second pitch, the forming of the joined part is performed by the processing apparatus as the certain process.

With such a manufacturing apparatus for manufacturing a composite sheet associated with an absorbent article, the joined part is formed on the substrate sheet, and the forming of the joined part is performed as the certain process in order to fix the substrate sheet in the two-folded state. Accordingly, the joined part can be formed on the substrate sheet precisely.

The extended state of the substrate sheet at the time of forming the joined part is the second extended state in which the substrate sheet has contracted from the first extended state. Accordingly, at the time of forming the joined part, the basis weight of the substrate sheet increases by an amount corresponding to the contraction. This makes it possible to increase the joining strength of the joined part.

In such a manufacturing apparatus for manufacturing a composite sheet associated with an absorbent article, it is desirable that concerning the substrate sheet that is in the second extended state and that is fixed in a two-folded state in which the substrate sheet is two-folded in a width direction of the substrate sheet, the processing apparatus produces the absorbent article by cutting the substrate sheet at the second pitch, the cutting is performed by the processing apparatus as the certain process.

With such a manufacturing apparatus for manufacturing a composite sheet associated with an absorbent article, the substrate sheet that is in second extended state and that is fixed in the two-folded state is cut at the second pitch to produce the absorbent article. This makes it possible to produce the absorbent article with high size precision.

In such a manufacturing apparatus for manufacturing a composite sheet associated with an absorbent article, it is desirable that an extension ratio of the substrate sheet in the first extended state remains at an extension ratio in the extended state at a time of the fixing process in the producing device in which the stretchable sheet is fixed to the low-extensible sheet, the low-extensible sheet when is fixed to the stretchable sheet that is in the extended state is extended and tightened, and the reference section is formed for each part of the substrate sheet, the part is a part that is to be the absorbent article.

With such a manufacturing apparatus for manufacturing a composite sheet associated with an absorbent article, in the first extended state, which is an extended state for forming the reference section on the substrate sheet, the stretchable sheet remains is in the extended state at the time of the fixing process in which the stretchable sheet is fixed to the low-extensible sheet. And, at the time of the fixing, the low-extensible sheet is extended and tightened. Accordingly, the reference section can effectively function as a more precise positional reference.

The reference section is formed for each part that is to be the absorbent article. Accordingly, each part that is to be the absorbent article can be subject to the certain process precisely. This makes it possible to finish each absorbent article with higher precision.

In such a manufacturing apparatus for manufacturing a composite sheet associated with an absorbent article, it is desirable that during a time period from the contraction in the contraction apparatus till the certain process, the sensor detects the reference section and outputs the detection signal.

With such a manufacturing apparatus for manufacturing a composite sheet associated with an absorbent article, the sensor detects the reference section and outputs the detection signal, during the time period from the contraction in the contraction apparatus till the certain process. This makes it possible to more quickly and more securely perform an adjustment according to the detection signal, the adjustment is performed by altering the transportation state of the substrate sheet so that the position in the substrate sheet for the certain process is located closer to a the target position in the substrate sheet for the certain process.

Further, a manufacturing method for manufacturing a composite sheet associated with an absorbent article, the manufacturing being performed by producing a substrate sheet and performing a certain process to the substrate sheet, the substrate sheet including a stretchable sheet and a low-extensible sheet, the low-extensible sheet having an extensibility lower than that of the stretchable sheet, the manufacturing method including:

producing the substrate sheet by fixing the stretchable sheet to at least the low-extensible sheet, the stretchable sheet continuing along a transporting direction, the stretchable sheet being transported, the stretchable sheet being in an extended state in which the stretchable sheet is extended in the transporting direction;

forming a physical reference section on the substrate sheet, the substrate sheet being in a first extended state and being transported;

causing the substrate sheet to contract in a contraction apparatus until the substrate sheet becomes in a second extended state whose extension ratio is smaller than an extension ratio of the first extended state, the substrate sheet having the reference section formed on it; and performing the certain process by a processing apparatus to the substrate sheet, the substrate sheet having contracted and being in the second extended state, causing the substrate sheet to contract including:

transporting the substrate sheet in a transport path;

detecting the reference section by a sensor and outputting a detection signal by a sensor after the contraction in the contraction apparatus; and altering a transportation state of the substrate sheet in the transport path so that a position in the substrate sheet for the certain process by the processing apparatus is located close to a target position for the certain process, the altering being performed according to the detection signal of the sensor.

With such a manufacturing method for manufacturing a composite sheet associated with an absorbent article, when the substrate sheet is in the first extended state in which the extension ratio is large, the reference section is formed on the substrate sheet. This makes it possible to form the reference section substantially without being affected by fluctuation of the contraction. Consequently, the reference section can be formed exactly at its target position in the substrate sheet. Thus, the reference section can effectively function as a positional reference on a substrate sheet.

The sensor detects the reference section after the contraction in the contraction apparatus, and outputs the detection signal. According to the detection signal, alteration device alters the transportation state of the substrate sheet in the transport path of the contraction apparatus. Thus, the position in the substrate sheet for the certain process is adjusted so as to be located close to its target position. Consequently, concerning the substrate sheet which has contracted in the contraction apparatus till the second extended state, the processing apparatus can perform a process exactly at its target position on the substrate sheet.

Present Embodiment

A manufacturing apparatus for a composite sheet associated with an absorbent article according to the present embodiment is used in a manufacturing line LM of pull-on disposable diapers 1, which is an example of the absorbent article.

Figure 2:
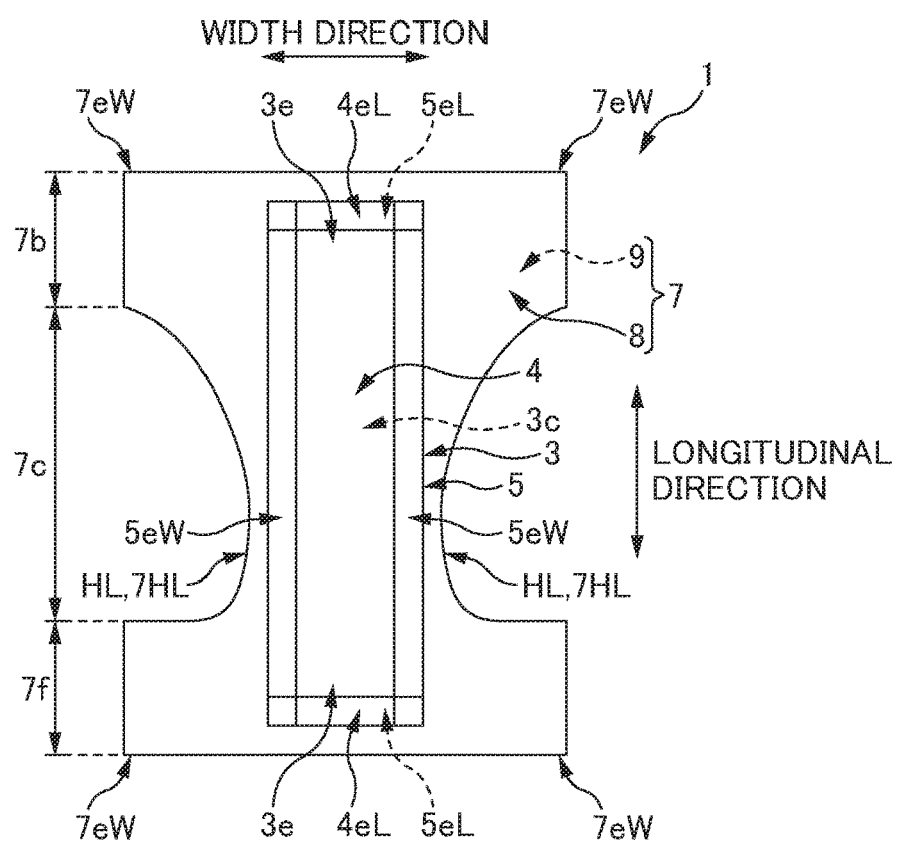
FIG. 2 is a schematic plan view of a diaper 1 which is spread out, as viewed from its skin side.
Figure 3:
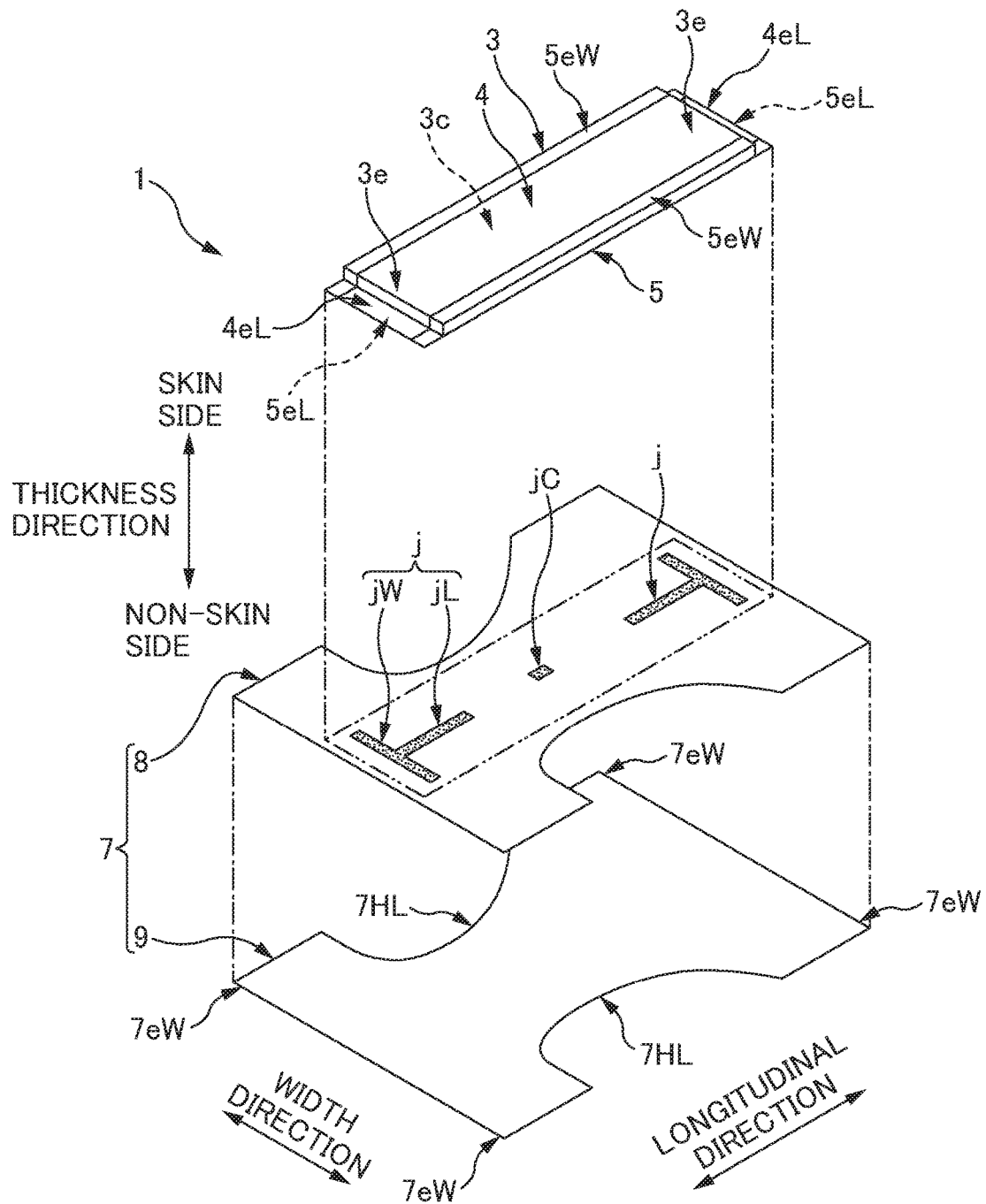
FIG. 3 is a schematic perspective view of the diaper 1 which is spread out and exploded.

FIG. 1 is a schematic perspective view of a pull-on diaper 1. FIG. 2 is a schematic plan view of the diaper 1 which is spread out, as viewed from its skin side. FIG. 3 is a schematic perspective view of the diaper 1 which is spread out and exploded.

In the description below, the side of a diaper 1 which should be located at the skin side of a wearer is merely referred to as a "skin side", and the side which should be located at the non-skin side of the wearer is merely referred to as a "non-skin side".

As shown in FIGS. 2 and 3, the diaper 1 is, for example, a diaper 1 consisting of two pieces. That is, the diaper 1 includes: an absorbent main body 3 in a substantially rectangular shape when viewed from above, as a first component, which absorbs excretion liquid such as urine; and an exterior sheet 7 in a substantially hourglass shape when viewed from above, as an second component, which covers the non-skin-side surface of the absorbent main body 3 and serves as an exterior of a diaper 1.

As shown in FIG. 3, the absorbent main body 3 includes an absorbent core 3c which absorbs excretion liquid. The absorbent core 3c is a body formed by shaping liquid-absorbent fiber (e.g. pulp fiber) or liquid-absorbent particles (e.g. superabsorbent polymer) into a predetermined shape (e.g. a substantially rectangular shape when viewed from above). Such an absorbent core 3c may be covered as necessary with a liquid-permeable cover sheet such as tissue paper.

On the skin-side surface of the absorbent core 3c, a liquid permeable top sheet 4 (e.g. nonwoven fabric) is provided so as to cover the surface. Also, on the non-skin-side surface of the absorbent core 3c, a liquid-impermeable leak-proof sheet 5 (e.g. film) is provided so as to cover the entire of the surface.

Here, in this example, both of the sheets 4 and 5 have a substantially rectangular shape when viewed from above, and extend and project outwardly from the longitudinal ends of the absorbent core 3c. The projecting parts 4eL of the top sheet 4 and the projecting parts 5eL of the leak-proof sheet 5 are respectively joined to each other by means such as adhesion or welding. In the width direction, the leak-proof sheet 5 extends and projects outwardly from both ends of the absorbent core 3c. These projecting parts 5eW and 5eW are folded back to the skin side, and are fixed by means such as adhesion or welding while covering the widthwise ends of the top sheet 4. Thus, the top sheet 4 and the leak-proof sheet 5 wrap the absorbent core 3c to form the absorbent main body 3.

Rubber threads (not shown) may be provided, as elastic members, in both widthwise ends of the absorbent main body 3 along the longitudinal direction of the absorbent main body 3. Such rubber threads are for providing stretchability to parts of the absorbent main body 3 and parts of the exterior sheet 7 in the vicinity of the leg openings HL. The rubber threads are placed, for example, between the top sheet 4 and the leak-proof sheet 5, and are fixed to these sheets 4 and 5 with adhesive (e.g. hot-melt adhesive) while being extended by a predetermined ratio (two to four times of its original unstretched length).

In some cases, leakage-proof walls (not shown) for preventing side leakage of urine may be provided in the absorbent main body 3. Such leakage-proof walls are so-called barrier cuffs. The barrier cuffs are configured by flexible sheets such as nonwoven fabric, and are provided, for example, on both ends of the skin-side surface of the absorbent main body 3 so as to stand. However, the leakage-proof wall is well known, and the description thereof will be omitted.

The exterior sheet 7 is a flexible sheet having a substantially hourglass shape when viewed from above in the state in which a diaper 1 is spread out as shown FIG. 2. The sheet 7 has three directions perpendicular to one another: the thickness direction; the longitudinal direction; and the width direction. The exterior sheet 7 is classified into three parts 7f, 7b and 7c in the longitudinal direction. That is, the exterior sheet 7 is classified into: a ventral part 7f arranged on the stomach side of a wearer; a dorsal part 7b arranged on the back side of a wearer; and a crotch part 7c arranged on the crotch of a wearer. It goes without saying that the crotch part 7c is located between the ventral part 7f and the dorsal part 7b. In a substantially hourglass shape when viewed from above, the crotch part 7c is a narrowed part 7c in the width direction.

As shown in FIG. 3, the exterior sheet 7 is made of a so-called laminated sheet 7 having a two-layer structure. That is, the exterior sheet 7 includes an inner-layer sheet 8 and an outer-layer sheet 9: the inner-layer sheet 8 faces the skin side of a wearer to serve as an inner layer; and the outer-layer sheet 9 faces the non-skin side of a wearer to serve as an outer layer. The inner-layer sheet 8 and the outer-layer sheet 9 are stacked in the thickness direction and are joined to each other by means such as adhesion or welding. In this example, welding is performed in a certain joining pattern (not shown) in which joined parts are discontinuously distributed.

The inner-layer sheet 8 is made of a stretchable sheet 8 having a stretchability in the width direction of a diaper 1. And, the outer-layer sheet 9 is made of a low-extensible sheet 9 having a low extensibility in the width direction of a diaper 1. The inner-layer sheet 8 having a stretchability is extended by a certain extension ratio corresponding to 2.5 times the original unstretched length in the width direction, for example (hereinafter referred to as an extended state), and the extended inner-layer sheet is stacked on the low extensible outer-layer sheet 9 which is stretched in the width direction. These sheets 8 and 9 are fixed to each other in the joining pattern in an integrated manner.

When the extended state is released, the inner-layer sheet 8 contracts in the width direction of the diaper 1 due to its stretchability. And, the outer-layer sheet 9 having a low extensibility bends in the width direction of the diaper 1 in the form of a plurality of creases. Thus, the outer-layer sheet 9 quickly follows the contraction of the inner-layer sheet 8, and the entire length of the outer-layer sheet 9 in the width direction decreases. Consequently, in a state in which external force is not exerted on a diaper 1, the entirety of the exterior sheet 7 shortens in the width direction, and simultaneously the outer surface of the exterior sheet 7 has a plurality of creases caused by the bending of the outer-layer sheet 9. However, pulling external force in the width direction is exerted on the exterior sheet 7, the exterior sheet 7 can extend almost elastically till the creases have completely stretched. That is, the exterior sheet 7 of a diaper 1 has a stretchability in the width direction.

The foregoing "stretchability" means a characteristic as follow: when pulling external force is exerted on an object, the object extends almost elastically in a direction in which the external force acts, and when the external force is released, the object contracts almost elastically. As mentioned above, a sheet having such a stretchability is the "stretchable sheet 8".

It is preferable that the stretchable sheet 8 satisfies the following conditions. That is, concerning a band-like sheet having a lateral length of 25 mm, while the longitudinal ends of the band-like sheet being held equally throughout the entire lateral length of 25 mm, the band-like sheet is pulled in the longitudinal direction with an external force of 1.0(N) which is applied on the longitudinal ends, and. Under this condition, it is preferable that the elongation ratio (%) of the band-like sheet is any value from 50% to 300%. Simultaneously, it is preferable that a residual elongation (%) which is elongation remaining after a sheet has contracted by releasing the external force is any value from 0% to 40%. It is more preferable that the elongation ratio is any value from 70% to 200% and simultaneously the residual elongation is any value from 0% to 30%. Here, the elongation ratio (%) is the percentage of a value (=ΔL1/L0) obtained by dividing a value ΔL1(=L1−L0) by an original unstretched length L0; the original unstretched length L0 is the length of a band-like sheet under no load which has not been pulled yet, and the value ΔL1(=L1−L0) is obtained by subtracting the original unstretched length L0 from the length L1 of a band-like sheet when the sheet is pulled with an external force of 1.0(N). The foregoing residual elongation (%) is the percentage of a value (=ΔL2/ΔL1) obtained by dividing value ΔL2 by the value ΔL1; the value ΔL2 (=L2−L0) is obtained by subtracting the original unstretched length L0 (before the pulling) from the length L2 (after the external force of 1.0(N) is released), and the value ΔL1 (=L1−L0) is obtained by subtracting the original unstretched length L0 from the length L1 when the sheet is pulled with the foregoing external force.

The "low-extensible sheet 9" is a sheet having an extensibility lower than that of the stretchable sheet 8. That is, the "low-extensible sheet 9" is a sheet whose elongation ratio (%) when a pulling external force of a certain magnitude is exerted on the sheet is lower than the elongation ratio (%) of the stretchable sheet 8. It is preferable that such a low-extensible sheet 9 satisfies the following conditions. That is, concerning a band-like sheet having a lateral length of 25 mm, while the longitudinal ends of the band-like sheet being held equally throughout the entire lateral length of 25 mm, the band-like sheet is pulled in the longitudinal direction with an external force of 1.0(N) which is applied on the longitudinal ends. Under this condition, it is preferable that the elongation ratio (%) of the band-like sheet is any value from 0% to 20%. It is more preferable that the elongation ratio is any value from 0% to 10%.

The stretchable sheet 8 and low-extensible sheet 9 may be made of nonwoven fabric or woven fabric or film.

A nonwoven fabric which can be used as the stretchable sheet 8 is exemplified by nonwoven fabric which is produced by a suitable elongation (e.g. gear elongation) of a nonwoven fabric, the nonwoven fabric including thermoplastic elastomer fibers showing substantial elasticity and thermoplastic resin fibers showing substantial inelasticity. That is, as a result of the elongation, the thermoplastic resin fibers showing substantial inelasticity and being contained in the nonwoven fabric can be subject to plastic deformation. In addition, breaking joints of the fibers makes it possible to change the structure of the nonwoven fabric to a structure which is less likely to prevent the almost elastic stretching deformation of the thermoplastic elastomer fibers. Consequently, the stretchability of the nonwoven fabric is produced and the sheet can be used as a stretchable sheet 8.

As a thermoplastic elastomer showing substantial elasticity, there are polyurethane elastomer, polystyrene elastomer, polyolefin elastomer, polyamide elastomer, and the like. As a thermoplastic resin fibers showing substantial inelasticity, there is fiber containing polyolefin resin and the like. The polyolefin resin is exemplified by polyethylene (PE), polypropylene (PP), ethylene-α-olefin copolymer, and the like. In this example, the stretchable sheet 8 is a sheet made of nonwoven fabric produced by gear elongation, the combined nonwoven fabric containing polyurethane elastomer fiber and PP fiber.

A nonwoven fabric which can be used as the low-extensible sheet 9 is exemplified by spunbond nonwoven fabric, melted-blown nonwoven fabric, air-through nonwoven fabric, so-called SMS nonwoven fabric (laminating spunbond nonwoven fabric, melted-blown nonwoven fabric, and spunbond nonwoven fabric) and the like, which are composed of fiber made of PE, PP, polyester, polyamid. The configuration of fibers is not limited to the foregoing single fiber made of one thermoplastic resin. For example, composite fiber having a core-sheath structure of a PP core and a PE sheath may be employed, and other types of the foregoing fibers may also be employed. In this example, spunbond nonwoven fabric made of PP fiber is used as a low-extensible sheet 9.

As shown in FIGS. 2 and 3, the foregoing absorbent main body 3 is attached to the skin-side surface of the exterior sheet 7 having the foregoing two-layer structure, that is, the body 3 is attached to the widthwise center on the skin-side surface of the inner-layer sheet 8. And the absorbent main body 3 is attached to the exterior sheet 7 so that the longitudinal direction of the absorbent main body 3 is aligned to the longitudinal direction of the exterior sheet 7. The attaching is made by joining at least the longitudinal ends 3e and 3e of the absorbent main body 3 to the exterior sheet 7. In this example, as shown in FIG. 3, on the longitudinal ends 3e and 3e, substantially T-shaped joined parts j and j are formed which join the absorbent main body 3 and the exterior sheet 7. That is, each of the joined parts j and j includes: a widthwise band-like part jW and a longitudinal band-like part jL. The widthwise band-like part jW is elongated in the width direction of the diaper 1, and the longitudinal band-like part jL extends toward the crotch part 7c from the widthwise central part of the widthwise band-like part jW. This makes it possible to effectively prevent the absorbent main body 3 and the exterior sheet 7 from unnecessarily constraining each other. However, the shape of the joined parts j is not limited thereto. For example, a spot of an additional joined part jC may be provided at a position between a pair of T-shaped joined parts j and j. Or, on each of the longitudinal ends 3e and 3e of the absorbent main body 3, a substantially rectangular joined part (not shown) having substantially the same area as the longitudinal end 3e may be formed. Or, a joined part having any other shape may be formed. In this example, forming of the joined parts j is achieved by adhesion with hot-melt adhesive. However, the invention is not limited thereto. For example, welding may be applied.

In this example, when attaching the absorbent main body 3 to the exterior sheet 7, the exterior sheet 7 is in a widthwise extended state in which the exterior sheet 7 is loosed compared to the inner-layer sheet 8 which is in an extended state at the time of fixing the outer-layer sheet 9 to the inner-layer sheet 8 (corresponding to a "reference extended state" and "first extended state" to be described later). The foregoing extended state in which the exterior sheet 7 is loosed is referred to as a "second extended state", and will be described later. Accordingly, when a pull-on diaper 1 is finally finished, the absorbent main body 3 is less likely to crease. This makes it possible to effectively prevent the foregoing troubles such as urine leakage and liquid-absorbency deterioration of the absorbent main body 3. In the below description of the manufacturing line LM, there is described that attaching of the absorbent main body 3 to the exterior sheet 7 is made in the extended state in which the sheet 7 is loosed.

The exterior sheet 7 to which the absorbent main body 3 is attached as shown in FIG. 2 is two-folded on its crotch part 7c. And, its ventral part 7f and its dorsal part 7b are stacked. The ventral part 7f and the dorsal part 7b which are stacked are joined on the widthwise ends 7eW, to be in a form of a pull-on diaper 1, in which a waist opening HB and a pair of leg openings HL and HL are formed as shown in FIG. 1.

FIG. 4A is a schematic side view of a manufacturing line LM which manufactures the foregoing diapers 1. FIG. 4B is a plan view showing how diapers 1 are manufactured in FIG. 4A.

First in this manufacturing line LM, the substrate sheet 7a of diapers 1 is produced. The substrate sheet 7a is continuously transported along a predetermined transporting direction by means such as suitable transport mechanisms CV, CV . . . . During the transportation, the substrate sheet 7a is subject to various processes such as attaching components or die-cutting. After every process, the substrate sheet 7a is sequentially processed, and a diaper 1 shown in FIG. 1 is finally manufactured. In this example, as shown in FIG. 4B, the substrate sheet 7a is transported basically in a so-called lateral-direction flowing. That is, the substrate sheet 7a is transported in a state in which a direction corresponding to the width direction of the diapers 1 is aligned to the transporting direction and a state in which pieces to be diapers 1 are lined up in the transporting direction.

As transport mechanisms CV which are used for the foregoing transportation, there are, for example, transport rollers, suction belt conveyors whose belt surfaces (serving as placement faces) have suction-holding function, or belt conveyors having pairs of upper and lower endless belts between which the transport path of the substrate sheet 7a is placed.

In the manufacturing line LM, a plurality of processing units 10, 20 . . . are arranged in the transporting direction for the various processes. In this example, as the plurality of processing units 10, 20 . . . , the manufacturing line LM includes: an exterior-sheet producing unit 10; a leg-opening forming unit 20; an exterior-sheet contraction unit 30; an absorbent-main-body attaching unit 40; a two-folding unit 50; an end-section sealing unit 60; and a dividing unit 70.

The processing units 10 to 70 will be described below, and in the description below, the transporting direction defined on the manufacturing line LM is referred to as "MD direction". One of two directions perpendicular to MD direction is referred to as "CD direction", and the other direction is referred to as "Z direction". CD direction is parallel to the width direction of the substrate sheet 7a, and is in a direction perpendicular to the paper plane in FIG. 4A. Z direction is parallel to the thickness direction of the substrate sheet 7a.

The exterior-sheet producing unit 10 (corresponding to the producing device), which is the first processing unit, produces a continuous sheet 7a of the exterior sheet 7 (hereinafter merely referred to as an exterior sheet 7a). The continuous sheet 7a is the substrate sheet 7a of the diapers 1, and continues in MD direction. That is, a stretchable sheet 8 (serving as the inner-layer sheet 8) is transported along MD direction, and a continuous sheet 8a of the stretchable sheet 8, which was in substantially an original unstretched length, extends in MD direction by a certain extension ratio (the continuous sheet 8a is hereinafter merely referred to as a "stretchable sheet 8a"). Simultaneously, the stretchable sheet 8a in the extended state is stacked on and joined to a continuous sheet 9a of low-extensible sheet 9 from the thickness direction, the continuous sheet 9a (the outer-layer sheet 9) being extended and tightened (the continuous sheet 9a is hereinafter merely referred to as a "low-extensible sheet 9a"). Consequently, the exterior sheet 7a is produced as the substrate sheet 7a.

For the purpose of producing the exterior sheet 7a, the exterior-sheet producing unit 10 includes: a transport mechanism 11 for the stretchable sheet 8a; a transport mechanism 13 for the low-extensible sheet 9a; and an ultrasonic welding device 15.

The main body of the transport mechanism 11 for the stretchable sheet 8a is, for example, a nip-roll mechanism. That is, the mechanism 11 includes a pair of nip rolls 11R and 11R which rotate respectively about rotational axes along CD direction. The pair of nip rolls 11R and 11R are driven and rotated by obtaining driving force from a servo motor (serving as a power source, not shown) while the stretchable sheet 8a, which is continuously transported from the upstream process, is being sandwiched between the outer circumferential surfaces of the nip rolls 11R and 11R. Thereby, the stretchable sheet 8a is transferred to the ultrasonic welding device 15.

On the other hand, the main body of the transport mechanism 13 for the low-extensible sheet 9a is, for example, a transport roller 13R which rotates about a rotational axis along CD direction. The transport roller 13R is driven and rotated by obtaining driving force from a servo motor (serving as a power source, not shown) while the outer circumferential surface of the roller 13R being in contact with the low-extensible sheet 9a, which is continuously transported from the upstream process. Thereby, the low-extensible sheet 9a is transferred to the ultrasonic welding device 15.

The ultrasonic welding device 15 includes: a horn 15h having a vibrating surface which vibrates ultrasonically; and an anvil roller 15a whose outer circumferential surface receives ultrasonic vibration of the vibrating surface of the horn 15h. The anvil roller 15a is supported being capable of rotating about a rotational axis along CD direction, and is driven and rotated by obtaining driving force from a servo motor (serving as a power source, not shown). The stretchable sheet 8a and the low-extensible sheet 9a, which have been transferred from the transport mechanisms 11 and 13, are wound around the outer circumferential surface of the anvil roller 15a at a certain wrapping angle (45° degrees or more) with substantially no sliding relative to the outer circumferential surfaces.

Accordingly, the anvil roller 15a is driven and rotated, and thereby the stretchable sheet 8a and the low-extensible sheet 9a are both transported, along the outer circumferential surface of the anvil roller 15a, at a conveying speed which is substantially same as the circumferential speed value V15a of the anvil roller 15a. The stretchable sheet 8a and the low-extensible sheet 9a pass the position of the horn 15h while the stretchable sheet 8a and the low-extensible sheet 9a being stacked in the thickness direction on the outer circumferential surface of the anvil roller 15a. At this stage, ultrasonic vibration energy is applied to these sheets 8a and 9a from the vibrating surface of the horn 15h, and these sheets 8a and 9a generate heat and melt. Thus, the sheets 8a and 9a are joined to each other in a joining pattern in which a plurality of the joined parts are discontinuously distributed. And, the exterior sheet 7a is consequently produced. The anvil roller 15a sends the exterior sheet 7a toward downstream in MD direction, and then the exterior sheet 7a is transported to the leg-opening forming unit 20 located downstream in MD direction, at a conveying speed which is substantially same as the circumferential speed value V15a.

Here, concerning the transport mechanism 11 of the stretchable sheet 8a, the circumferential speed value V11R (m/min.) of the nip roll 11R is substantially same as the conveying speed (m/min.) of the stretchable sheet 8a which is transported from the upstream process, the stretchable sheet 8a being in substantially the original unstretched length. On the other hand, the circumferential speed value V15a (m/min.) of the anvil roller 15a, being located downstream thereof, is set to a value of the circumferential speed value V11R (m/min.) of the nip roll 11R multiplied by the extension ratio. Accordingly, when the stretchable sheet 8a passes between the nip-roll mechanism 11 and the anvil roller 15a, the stretchable sheet 8a extends from the original unstretched length till the length corresponding to the extension ratio. The stretchable sheet 8a passes the position of the horn 15h in the extended state. On the other hand, concerning the transport mechanism 13 of the low-extensible sheet 9a, the circumferential speed value V13R (m/min.) of the transport roller 13R is substantially same as the conveying speed (m/min.) of the low-extensible sheet 9a which is transported from the upstream process. The conveying speed (m/min.) is also substantially same as the circumferential speed value V15a (m/min.) of the anvil roller 15a. Accordingly, the low-extensible sheet 9a remains in a state in which the sheet 9a is properly extended and tightened to substantially an extent that does not undergo plastic deformation or the like. On the anvil roller 15a, the low-extensible sheet 9a which has been extended and tightened is stacked on and joined to the stretchable sheet 8a which has extended till the length corresponding to the extension ratio.

The low-extensible sheet 9a which is extended and tightened is in a so-called fully-extended state in which a sheet having a low extensibility is difficult to further extend. Accordingly, even if an unexpectedly great tension is exerted during subsequent transportation, the low-extensible sheet 9a can resist the tension so that the length of the exterior sheet 7a in MD direction does not change. Accordingly, the subsequent forming of the leg opening 7HL in the exterior sheet 7a can be made with high positioning accuracy. The foregoing "fully-extended state" can be defined as, for example, "a state in which a sheet is not damaged and cannot further extend from the current state at the elongation ratio of 5% or more with its sheet-like shape being kept".

The foregoing "extension ratio" indicates how many times as long as the original unstretched lengths of the stretchable sheet 8a the entire length of the sheet 8a in an extended state is. And, the "extension ratio" defines how much the exterior sheet 7 (7a) of a finished diaper 1 can extend in the width direction from a state in which no force is exerted on the sheet 7 (7a). That is, in a diaper 1 which has been manufactured when the setting of the stretchable sheet 8a is in a certain extension ratio, the exterior sheet 7 (7a) can extend in the width direction of a diaper 1 till the extended state, corresponding to the foregoing extension ratio. The extension ratio is set, for example, to any value from 1.5 times to 4 times. In this example, the extension ratio is predetermined to 2.5 times. In the description below, a state in which the stretchable sheet 8a extends by the exterior-sheet producing unit 10 till the predetermined extension ratio is referred to as a "reference extended state".

In the leg-opening forming unit 20 in the next process, the extended state of the exterior sheet 7a remains in the reference extended state mentioned above. That is, the exterior sheet 7a is transported in an extended state in which the exterior sheet 7a extends at an extension ratio of 2.5 that is the same as the extension ratio in the reference extended state (hereinafter referred to as a first extended state). In the leg-opening forming unit 20, the exterior sheet 7a in the first extended state is being transported, and the leg opening 7HL is cut out and formed by die-cutting the exterior sheet 7a at a certain first pitch P1 (corresponding to the first pitch).

Here, such a first pitch P1 corresponds to the length in MD direction of a single diaper 1 which is in the first extended state. Accordingly, in the exterior sheet 7a, a single leg opening 7HL is formed for every part corresponding to a diaper 1. The length of a single diaper 1 varies depending on an extended state of the exterior sheet 7a. For example, if the exterior sheet 7a contracts and is in a looser extended state, the length in MD direction of a single diaper 1 shortens by a length corresponding to the contraction.

The forming the leg opening 7HL is performed by a die cutter device 21. The die cutter device 21 includes a pair of upper and lower rolls 21u and 21d which rotate respectively about rotational axes along CD direction while their outer circumferential surfaces facing each other. The upper roll 21u is a cutter roll 21u having a cutter blade 21c on the outer circumferential surface. And, the lower roll 21d is an anvil roll 21d which receives the cutter blade 21c on its smooth outer circumferential surface. The cutter blade 21c is a so-called annular cutting die whose shape corresponds to the shape of the leg opening 7HL. The cutter blade 21c is provided protruding from the outer circumferential surface 21us of the cutter roll 21u. Accordingly, when the exterior sheet 7a passes the nip between the upper and lower rolls 21u and 21d, the section of the exterior sheet 7a which is located inside the annular cutter blade 21c is cut out from the exterior sheet 7a by die-cutting. Consequently, a leg opening 7HL is formed in the exterior sheet 7a.

In this example, the power source by which the upper and lower rolls 21u and 21d are driven and rotated is a servo motor (not shown). The upper roll 21u includes a single cutter blade 21c on its outer circumferential surface. Accordingly, every time when the exterior sheet 7a passes the die cutter device 21 by the length of the first pitch P1 in MD direction, the upper roll 21u and the lower roll 21d rotate once and the leg openings 7HL are thereby formed in the exterior sheet 7a at the first pitch P1. Thus, the leg openings 7HL are formed in the exterior sheet 7a at a pitch corresponding to the length of a single diaper 1 which is in the first extended state.

In order to perform die-cutting with substantially no sliding relative to the exterior sheet 7a, the rotation radius at the position of the cutting edge of the cutter blade 21c is defined based on the first pitch P1 at which the leg openings 7HL are to be formed. Similarly, the rotation radius of the outer circumferential surface of the lower roll 21d is defined based on the first pitch P1. That is, the rotation radius at the position of the cutting edge of the upper roll 21u and the rotation radius of the outer circumferential surface of the lower roll 21d are set to a value obtained by dividing the first pitch P1 by 2n (two times pi). This enables the die cutter device 21 to form the leg openings 7HL precisely at the first pitch P1, in the exterior sheet 7a which is in the first extended state. Then, the exterior sheet 7a which is in the first extended state is transferred to the exterior-sheet contraction unit 30 downstream in MD direction.

In the exterior-sheet contraction unit 30 (corresponding to the contraction apparatus) in the next process, the exterior sheet 7a which is being transported in the first extended state contracts in MD direction. Consequently, the exterior sheet 7a becomes in an extended state (hereinafter referred to as a second extended state) in which the extension ratio is smaller than the extension ratio in the first extended state. In this example, the extension amount of the exterior sheet 7a is reduced so that the extension ratio is 2.25 times. That is, the extension amount is reduced by 10% of 2.5 times, which is the extension ratio in the first extended state. This prevents possible creasing of the absorbent main body 3, which will be subsequently attached to the exterior sheet 7a. Hereinafter, the extension ratio in the first extended state is referred to as a "first extension ratio M1", and the extension ratio in the second extended state is referred to as a "second extension ratio M2".

The foregoing contraction of the exterior sheet 7a is performed by two nip-roll mechanisms 31 and 33 provided being lined up in MD direction. That is, the upstream nip-roll mechanism 31 is arranged at a predetermined position in MD direction, and the downstream nip-roll mechanism 33 is arranged at a position downstream from the upstream nip-roll mechanism 31. These nip-roll mechanisms 31 and 33 have substantially the same configuration.

That is, the upstream nip-roll mechanism 31 includes a pair of upper and lower nip rolls 31u and 31d which rotate respectively about rotational axes along CD direction. Also, the downstream nip-roll mechanism 33 includes a pair of upper and lower nip rolls 33u and 33d which rotate respectively about rotational axes along CD direction. The pair of nip rolls 31u and 31d of the upstream nip-roll mechanism 31 are driven and rotated by obtaining driving force from a servo motor (serving as a power source, not shown) while the exterior sheet 7a is being sandwiched between the outer circumferential surfaces of the nip rolls 31u and 31d. Thereby, the exterior sheet 7a is transferred downstream in MD direction. Similarly, the pair of nip rolls 33u and 33d of the downstream nip-roll mechanism 33 are driven and rotated by obtaining driving force from a servo motor (serving as a power source, not shown) while the exterior sheet 7a is being sandwiched between the outer circumferential surfaces of the nip rolls 33u and 33d. Thereby, the exterior sheet 7a is transferred further downstream in MD direction.

Here, the circumferential speed value V31 (m/min.) of the nip rolls 31u and 31d of the upstream nip-roll mechanism 31 is substantially same as the circumferential speed value V15a (m/min.) of the anvil roller 15a of the foregoing ultrasonic welding device 15. Accordingly, the circumferential speed value V31 of the nip rolls 31u and 31d is substantially same as the first conveying speed of the exterior sheet 7a, which is the conveying speed (m/min.) of the exterior sheet 7a which is being transported in the first extended state at a position immediately upstream from the nip rolls 31u and 31d. On the other hand, the circumferential speed value V33 (m/min.) of the nip rolls 33u and 33d of the downstream nip-roll mechanism 33 is smaller by 10% than the circumferential speed value V31 of the nip rolls 31u and 31d of the upstream nip-roll mechanism 31. Accordingly, while the exterior sheet 7a is passing the transport path R30 between the upstream nip-roll mechanism 31 and the downstream nip-roll mechanism 33, the exterior sheet 7a contracts to be in the second extended state; the extension ratio in the second extended state being smaller by 10% than the extension ratio in the first extended state. The exterior sheet 7a in the second extended state is transported to the absorbent-main-body attaching unit 40 located downstream in MD direction.

In this example, when the exterior sheet 7a is being transported during and after the contracting, the exterior sheet 7a is basically in substantial a second extended state. During the transportation, the conveying speed of the exterior sheet 7a is kept at approximately a conveying speed (hereinafter referred to as a second conveying speed) which is smaller than the first conveying speed by 10% (the ratio corresponding to the contraction). The second conveying speed can be also referred to as "a value obtained by multiplying the first conveying speed by a value obtained by dividing the second extension ratio by the first extension ratio".

Here, the contraction ratio (%) is a value indicating the degree of the contraction of the exterior sheet 7a, and is defined as follow. The contraction ratio (%) is the percentage of a divided value (=(M1−M2)/M1) obtained by dividing a subtraction value (=M1−M2) by the first extension ratio M1, the subtraction value being obtained by subtracting the second extension ratio M2 from the first extension ratio M1. In this example, as mentioned above, the contraction ratio is 10%. However, this invention is not limited thereto. That is, the contraction ratio may be set to any value as long as the exterior sheet 7a can contract while being extended and tightened; for example, the contraction ratio may be any value from 2% to 80%. As a narrower example, the contraction ratio may be any value from 5% to 50%, or as a further narrower example, the contraction ratio may be any value from 7% to 30%.

In the absorbent-main-body attaching unit 40 (corresponding to a processing apparatus) in the next process, the exterior sheet 7a is being transported in the second extended state, and the absorbent main body 3 is attached to the exterior sheet 7a at a second pitch P2 (corresponding to the second pitch) in MD direction. Here, such a second pitch P2 corresponds to the length in MD direction of a single diaper 1 which is in the second extended state. In the second extended state, the exterior sheet 7a contracts more than in the first extended state, as mentioned above. Accordingly, the second pitch P2 is a smaller value than the first pitch P1 by the contraction ratio. Specifically, in this example, though the first extension ratio of the first extended state is 2.5, the second extension ratio of the second extended state is reduced and is 2.25. Accordingly, the contraction ratio is 10% (=(2.5−2.25)/2.5×100%), and the second pitch P2 of the absorbent-main-body attaching unit 40 is a smaller value than the first pitch P1 by 10%.

The absorbent main body 3 is attached to the exterior sheet 7a at a position between leg openings 7HL and 7HL which are adjacent in MD direction. In the present embodiment, the transportation of the exterior sheet 7a in the foregoing exterior-sheet contraction unit 30 is adjusted so that the absorbent main body 3 is attached to the exterior sheet 7a at a predetermined target position. The adjustment is performed by an adjustment device 35, which will be described later.

The attaching of the absorbent main body 3 is performed by, for example, a rotating-drum device 41. The rotating-drum device 41 includes: a rotating drum 42 which rotates about a rotational axis along CD direction; a servo motor (not shown) which serves as a power source and which drives and rotates the rotating drum 42; and a plurality of holding pads 43, 43 . . . provided along the rotating direction on the outer circumferential surface of the rotating drum 42. Each holding pad 43 has a holding plane which is capable of sucking and holding the absorbent main body 3, and the holding plane faces outside in the rotation radius of the rotating drum 42. By the rotation of the holding pad 43 about the axis which is located at the plane center of its holding plane, the longitudinal direction of an absorbent main body 3 held by the holding plane changes from MD direction to CD direction.

Each holding pad 43 is configured so as to reciprocate relative to the rotating drum 42 within a certain range in the rotating direction. Such a reciprocating motion is produced by a suitable cam mechanism (not shown) from a rotation of the rotating drum 42. Accordingly, a pitch in the rotating direction between adjacent holding pads 43 and 43 can be changed depending on the position of the rotating drum 42 in the rotating direction. That is, at a first position S1 in the rotating direction, a space between adjacent holding pads 43 and 43 can be narrow, and at a second position S2 in the rotating direction, a space between adjacent holding pads 43 and 43 can be wide.

Here, at the first position S1, a plurality of the absorbent main bodies 3 are supplied in the form of continuous body 3a which continues in MD direction. When each holding pad 43 passes the first position S1, the pad 43 sucks and receives the continuous body 3a of the absorbent main body. And then, the cutter apparatus 45 located near the pad 43 divides the continuous body 3a, and a single sheet of the absorbent main body 3 is produced on the holding pad 43. The holding pad 43, as it is, moves to the second position S2 in the rotating direction by rotation of the rotating drum 42. During the movement, the holding pad 43 rotates as mentioned above, and the longitudinal direction of the absorbent main body 3 is thereby changed from MD direction to CD direction. In addition thereto, the holding pad 43 reciprocates during the movement, and a pitch between adjacent holding pads 43 and 43 is thereby changed to the second pitch P2. Further, at the second position S2, the transport path of the exterior sheet 7a is placed closely to the unit 40. Accordingly, the rotating-drum device 41 can attach the absorbent main bodies 3, at the second pitch P2 in MD direction, to the exterior sheet 7a which is in the second extended state.

In the two-folding unit 50 in the next process, the exterior sheet 7a onto which the absorbent main bodies 3 are attached is two-folded in CD direction at a folding position, which is substantially a central part of the exterior sheet 7a in CD direction corresponding to the crotch part 7c of a diaper 1. Thus, in the exterior sheet 7a, one end section of the sheet 7a in CD direction is stacked on the other end section in the thickness direction. One end section finally becomes the ventral part 7f of a diaper 1, and other end section finally becomes the dorsal part 7b of the diaper 1.

The two-folding of the exterior sheet 7a is performed by a two-fold guiding member (not shown) arranged at a predetermined position in MD direction. The two-fold guiding member is a known configuration, and is composed of a combination of a plurality of suitable bars, for example. When the exterior sheet 7a passes the position of the two-fold guiding member, the guiding member folds gradually the exterior sheet 7a at the folding position, which is substantially a central part of the exterior sheet 7a in CD direction. When the exterior sheet 7a has completely passed the two-fold guiding member, the exterior sheet 7a is two-folded.

In the two-folding unit 50, the extended state of the exterior sheet 7a remains the second extended state mentioned above. While the exterior sheet 7a remaining in this extended state, the exterior sheet 7a is transferred downstream in MD direction. That is, in the two-folding unit 50, the conveying speed of the exterior sheet 7a is kept substantially same as the foregoing second conveying speed.

In the next end-section sealing unit 60 (corresponding to the processing apparatus), the exterior sheet 7a remains in the second extended state. In the end-section sealing unit 60, the exterior sheet 7a that has been two-folded is fixed in a state in which the exterior sheet 7a is two-folded. That is, the end sections of the exterior sheet 7a in CD direction, which are stacked by being two-folded in the thickness direction, are welded at a position in MD direction between adjacent absorbent main bodies 3 and 3. And, the end sections are fixed in the state in which the exterior sheet 7a is two-folded. The welded part remains on the exterior sheet 7a, as a sealed end section jes (corresponding to the joined part). At a position where the sealed end section jes is to be formed, the exterior sheet 7a is in the second extended state. And, the welded parts are produced at the second pitch P2 in MD direction. Accordingly, the unit 60 forms the sealed end sections jes at the second pitch P2 in the exterior sheet 7a.

The forming of the sealed end section jes is performed by a heat-sealing device 61. The heat-sealing device 61 includes a pair of upper and lower rolls 61u and 61d which are driven and rotated about rotational axes along CD direction while their outer circumferential surfaces facing each other.

The upper roll 61u has a sealing pattern section 61sp on its outer circumferential surface. The sealing pattern section 61sp is a protrusion and is heated. The lower roll 61d has a smooth outer circumferential surface, which is for receiving the sealing pattern section 61sp. The sealing pattern section 61sp protrudes from the outer circumferential surface of the upper roll 61u, and the protruding part has a shape corresponding to a sealed end section jes. Accordingly, when the two-folded exterior sheet 7a passes the nip between the upper and lower rolls 61u and 61d, a part of the exterior sheet 7a between the absorbent main bodies 3 and 3 which are adjacent in MD direction is heated while being pressed between a sealing pattern section 61sp and the outer circumferential surface of a lower roll 61d. Thus, a part of the exterior sheet 7a which is to be a widthwise end of each diaper 1 is melted, and the sealed end section jes is formed in the melted part.

In this example, the power source by which the upper and lower rolls 61u and 61d are driven and rotated is a servo motor (not shown). A single sealing pattern section 61sp is provided on the outer circumferential surface of the upper roll 61u. Every time when the exterior sheet 7a passes the heat-sealing device 61 by the length of the second pitch P2, the upper roll 61u rotates once. Accordingly, the sealed end sections jes are formed at the second pitch P2. Consequently, in the exterior sheet 7a, the sealed end sections jes are formed at a pitch corresponding to the length of a single diaper 1 which is in the second extended state.

In order to form the sealed end section jes with substantially no sliding relative to the exterior sheet 7a, the rotation radius at the position of the top surface of the sealing pattern section 61sp is defined based on the second pitch P2 at which the sealed end sections jes are to be formed. Similarly, the rotation radius of the outer circumferential surface of the lower roll 61d is defined based on the second pitch P2. That is, the rotation radius at the position of the sealing pattern section 61sp of the upper roll 61u, and the rotation radius of the outer circumferential surface of the lower roll 61d are set to a value obtained by dividing the second pitch P2 by 2n (two times pi). This enables the heat-sealing device 61 to form the sealed end sections jes precisely at the second pitch P2, in the exterior sheet 7a which is in the second extended state. Then, the exterior sheet 7a which is in the second extended state is transferred to the dividing unit 70 downstream in MD direction.

The extended state of the exterior sheet 7a at the time of forming the sealed end section jes is the second extended state as mentioned above. The second extended state is a state in which a sheet being in the first extended state contracts. Accordingly, when forming the sealed end section jes, the basis weight (g/m$^2$) of the exterior sheet 7a increases by an amount corresponding to the foregoing contraction. This makes it possible to increase welding strength of the sealed end section jes.

In the next dividing unit 70 (corresponding to the processing apparatus), the exterior sheet 7a remains in the second extended state. The exterior sheet 7a which is two-folded and fixed is divided at the second pitch P2. Consequently, the downstream end part of the exterior sheet 7a is cut and separated from the sheet 7a at the second pitch P2 to produce a diaper 1.

The dividing of the exterior sheet 7a is performed by a rotary cutter device 71. The rotary cutter device 71 includes a pair of upper and lower rolls 71u and 71d which are driven and rotated about rotational axes along CD direction while their outer circumferential surfaces facing each other. The upper roll 71u is a cutter roll 71u having a cutter blade 71c on its outer circumferential surface, and the lower roll 71d is an anvil roll 71d having a smooth outer circumferential surface, which receives the cutter blade 71c. The cutter blade 71c is, for example, a flat blade extending along CD direction, and protrudes from the outer circumferential surface of the cutter roll 71u. When the exterior sheet 7a which is two-folded and fixed passes a nip between these upper and lower rolls 71u and 71d, the exterior sheet 7a is divided at the position of the sealed end section jes. Consequently, the downstream end part of the exterior sheet 7a is cut and separated from the sheet 7a, and the separated downstream end part becomes a diaper 1.

In this example, the power source by which the upper and lower rolls 71u and 71d are driven and rotated is a servo motor (not shown). A single cutter blade 71c is provided on the outer circumferential surface of the upper roll 71u. The exterior sheet 7a is transported being in the second extended state. Every time when the exterior sheet 7a passes the rotary cutter device 71 by the length of the second pitch P2, the upper roll 71u and the lower roll 71d each rotate once. Accordingly, from the exterior sheet 7a, a single diaper 1 is divided and produced. The produced diaper 1 is transferred downstream in MD direction by a suitable transport mechanism CV such as a belt conveyor.

In order to divide the exterior sheet 7a with substantially no sliding relative to the exterior sheet 7a, the rotation radius at the position of the cutting edge of the cutter blade 71c is defined based on the second pitch P2 at which the exterior sheet 7a are to be divided. Similarly, the rotation radius of the outer circumferential surface of the lower roll 71d is defined based on the second pitch P2. That is, the rotation radius at the position of the cutting edge of the upper roll 71u and the rotation radius of the outer circumferential surface of the lower roll 71d are set to a value obtained by dividing the second pitch P2 by 2n (two times pi). This enables the rotary cutter device 71 to divide the exterior sheet 7a precisely at the second pitch P2, the exterior sheet 7a being in the second extended state.

The processing units 10 to 70 included in the manufacturing line LM are described above. The processing units 10 to 70 operate in conjunction with one another. There are two methods of the operation conjunction, for example. The one is a method in which the operation conjunction is achieved by controlling the positions of target apparatuses based on synchronization signals, and the other is a method in which the operation conjunction is achieved by controlling the speeds of target apparatuses.

The former method using synchronization signals is applied to the leg-opening forming unit 20, the absorbent-main-body attaching unit 40, the end-section sealing unit 60 and the dividing unit 70.

The synchronization signal is a signal consisting of a unit signal which corresponds to a unit part of the exterior sheet 7a which is to be a diaper 1; the unit signal is repeatedly outputted. In this example, the unit signal is a rotational angle signal having a rotational angle value of 0° to 360°.

The processing units 20, 40, 60 and 70 each have a systematic unit operation which they should repeatedly perform for each unit part of the exterior sheet 7a which is to be a diaper 1. The unit operation of each of the processing units is in one-to-one correspondence with a single unit signal.

The synchronization signal is transmitted to an amplifier of each of servo motors, which are power sources of the devices 21, 41, 61 and 71 of the processing units 20, 40, 60 and 70. And, the positions of the servo motors are controlled based on the synchronization signal. Thus, each of the devices 21, 41, 61 and 71 performs its predetermined unit operation, to unit parts of the exterior sheet 7a, which are to be a diaper 1.

For example, in the leg-opening forming unit 20, the upper and lower rolls 21u and 21d of the die cutter device 21 each rotate once as a unit operation according to position control, and this operation is performed for each unit signal of the synchronization signal. Thus, the leg openings 7HL are formed on the exterior sheet 7a at the first pitch P1. In the absorbent-main-body attaching unit 40, the rotating drum 42 of the rotating-drum device 41 attaches, as a unit operation, the absorbent main body 3 to the exterior sheet 7a at the second pitch P2 according to position control, and this operation is performed for each unit signal. In the end-section sealing unit 60, the upper and lower rolls 61u and 61d of the heat-sealing device each rotate once as a unit operation according to position control, and this operation is performed for each unit signal. Thus, the sealed end sections jes are formed on the exterior sheet 7a at the second pitch P2. In the dividing unit 70, the upper and lower rolls 71u and 71d of the rotary cutter device 71 each rotate once as a unit operation according to position control. Thus, the exterior sheet 7a is divided at the second pitch P2, to produce a diaper 1.

The synchronization signal is generated by a controller (not shown) which controls the processing units 20, 40, 60 and 70 in the manufacturing line LM, for example. The controller includes a processor and a memory, and in the memory, the program that generates the synchronization signal is stored in advance. The processor reads the program from the memory and executes it, and thereby repeatedly generates a unit signal of the synchronization signal.

For the purpose of explanation, in this example, the unit signal of the synchronization signal is a signal indicated by a rotational angle value of 0° to 360°. However, this invention is not limited thereto. For example, the unit signal of the synchronization signal may be a digital value (e.g. from 0 to 8191). Or, the synchronization signal may be generated by a suitable electric circuit, not by the processor which has read the foregoing program.

On the other hand, the latter method using speed control is applied to the exterior-sheet producing unit 10, the exterior-sheet contraction unit 30, and the transport mechanisms CV, CV . . . . In such a method, a reference speed value is set to the speed value (m/min.) of a core unit or the target value (m/min.) of the same. A target speed value (m/min.) is obtained by means such as multiplying the reference speed value by a suitable gain. The speed value (m/min.) of the other cooperating units is controlled so as to be close to the target speed value.

In this example, the core unit is the die cutter device 21 of the leg-opening forming unit 20. And, the reference speed value Vs is the circumferential speed value V21 (m/min.) of the lower roll 21d of the die cutter device 21. In the exterior-sheet producing unit 10, the circumferential speed value V15a of the anvil roller 15a is controlled so as to be a target speed value, which is the reference speed value Vs.

In the exterior-sheet producing unit 10, concerning the transport roller 13R of the transport mechanism 13 for the low-extensible sheet 9a, the circumferential speed value V13R is controlled so as to be a target speed value, which is the reference speed value. Further, in the exterior-sheet producing unit 10, concerning the pair of nip rolls 11R and 11R of the transport mechanism 11 for the stretchable sheet 8a, each of the circumferential speed values V11R and V11R is controlled so as to be a target speed value, which is a multiplied value obtained by multiplying the reference speed value Vs by the reciprocal of the extension ratio at the time when the sheets 8 and 9 are fixed (serving as a gain; in this example, 2.5 times).

In the exterior-sheet contraction unit 30, concerning the pair of nip rolls 31u and 31d of the upstream nip-roll mechanism 31, each of the circumferential speed values V31u and V31d is controlled so as to be a target speed value, which is the reference speed value Vs. Concerning the pair of nip rolls 33u and 33d of the downstream nip-roll mechanism 33, each of the circumferential speed values V33u and V33d is controlled so as to be a target speed value, which is a value obtained by multiplying the reference speed value Vs by a certain gain G. The gain G is a divided value obtained by dividing a subtraction value by 100, the subtraction value being obtained by subtracting the contraction ratio (%) from 100%. In this example, the gain G is 0.9 (=(100−10)/100).

Taking into consideration the extended state of the exterior sheet 7a, the target speed value of each of the transport mechanisms CV, CV . . . is obtained based on the foregoing reference speed value Vs. Concerning the transport mechanism CV, the circumferential speed value of its transport roller or its endless belt is controlled according to the target speed value. That is, concerning a transport mechanism CV transporting the exterior sheet 7a which is in the first extended state, the circumferential speed value of its transport roller or its endless belt is controlled so as to be a target speed value, which is the reference speed value Vs. On the other hand, concerning a transport mechanism transporting the exterior sheet 7a which is in the second extended state, its circumferential speed value is controlled so as to be a target speed value, which is a multiplied value obtained by multiplying the reference speed value Vs by the foregoing gain G associated with the contraction.

Under such a control for cooperation, in the exterior-sheet contraction unit 30 of the manufacturing line LM, the exterior sheet 7a contracts in MD direction as mentioned above. But, because of variation in the stretchability of the exterior sheet 7a or the like, the contraction may cause a problem that a target position for each process, which is determined on the exterior sheet 7a, is shifted upstream or downstream in MD direction relative to an actual position at which a process by each of the processing units 40, 60 and 70 is made according to the synchronization signal.

For example, concerning a certain part of the exterior sheet 7a, its contraction is larger than expected, the exterior sheet 7a is transported in which the position of the certain part is shifted toward upstream in MD direction from its transportation position which is determined according to the synchronization signal. Consequently, a process by each of the processing units 40, 60 and 70 according to the synchronization signal is made at a position located downstream from the target position for the process, which is determined in the certain part of the exterior sheet 7a. On the other hand, the contraction is smaller than expected, the opposite of the foregoing description will happen. That is, there is generated a shifting amount, which indicates difference between the following positions: an actual position at which a process by each of the processing units 40, 60 and 70 is made according to the synchronization signal; and a target position determined on the exterior sheet 7a.

Figure 5A:
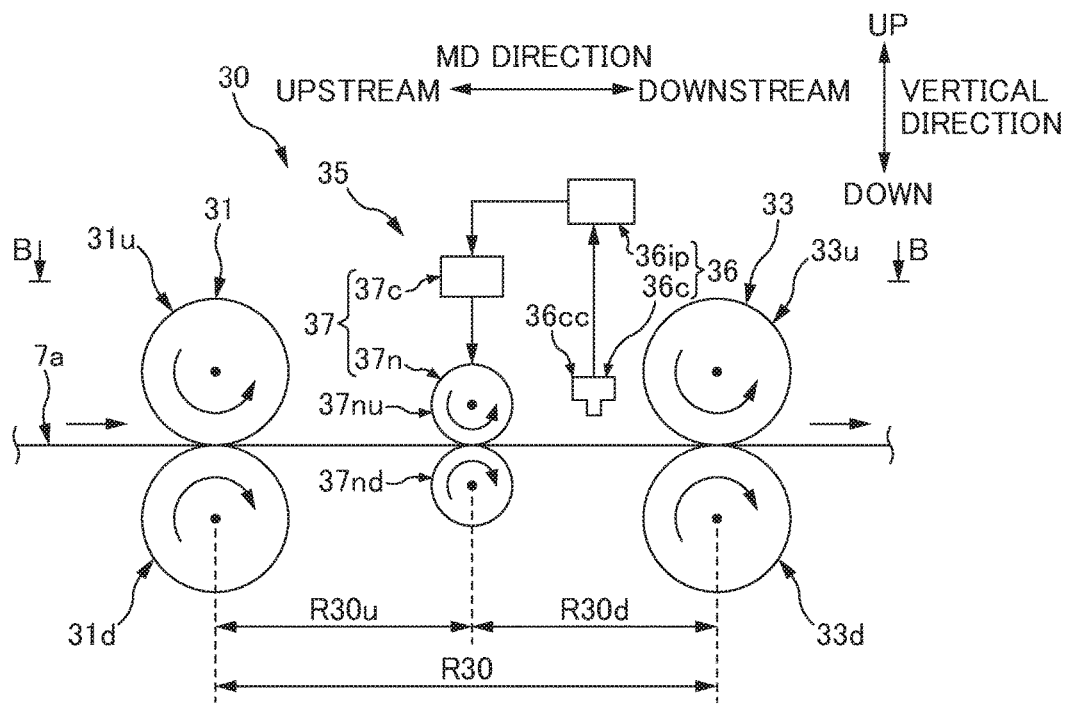
FIG. 5A is a schematic side view of an exterior-sheet contraction unit 30 including an adjustment device 35 according to the present embodiment.
Figure 5B:
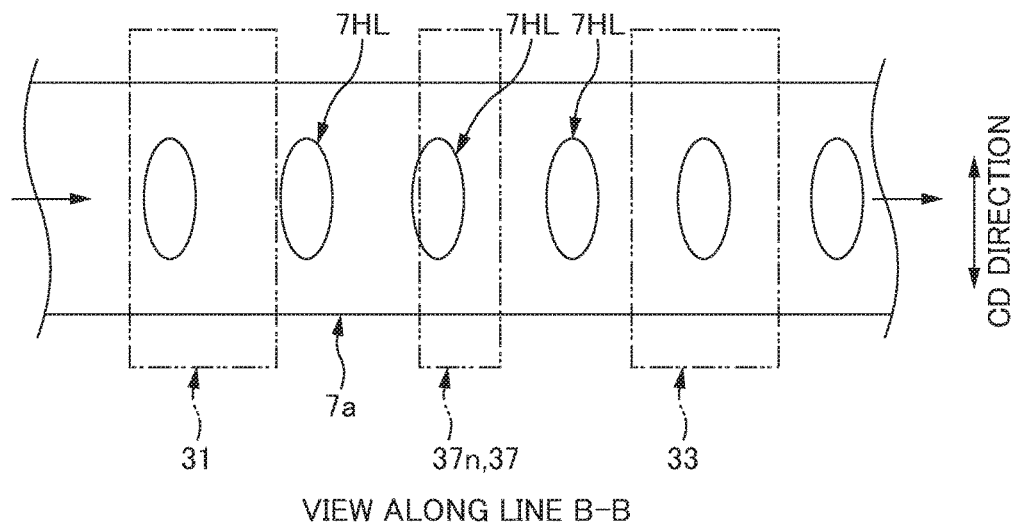
FIG. 5B is a schematic view along arrows B-B in FIG. 5A.

In the present embodiment, the adjustment device 35 is provided for reducing the foregoing shifting amount. FIG. 5A is a schematic side view of the exterior-sheet contraction unit 30 including the adjustment device 35. FIG. 5B is a schematic view along arrows B-B in FIG. 5A.

The adjustment device 35 includes a sensor 36 and an alteration device 37. The sensor 36 detects a physical reference section and outputs a detection signal. The physical reference section is a section in the exterior sheet 7a and is formed for each unit part of the exterior sheet 7a which is to be a diaper 1. The alteration device 37 alters the transportation state of the exterior sheet 7a when the exterior sheet 7a is in the transport path R30 in the exterior-sheet contraction unit 30. The alteration device 37 alters the transportation state of the exterior sheet 7a in the exterior-sheet contraction unit 30, and the alteration is performed according to the detection signal outputted from the sensor 36. And, the alteration is made so that positions in the exterior sheet 7a for processes made by the processing units 40, 60 and 70 located downstream in MD direction (that is, positions for the processes determined according to the synchronization signal) is located close to the target position which is defined on the exterior sheet 7a. The detail will be described below.

In this example, the leg opening 7HL is used as the reference section. This is because it can be considered that forming of each leg opening 7HL under a stable condition ensures a high positioning accuracy of the leg opening 7HL and that the forming of each leg opening 7HL is performed under a condition in which the 10% contraction of the exterior sheet 7a has not been made yet, that is, under a stable condition in which the exterior sheet 7a extends almost as much as possible (in the first extended state). In this case, the foregoing leg-opening forming unit 20 corresponds to the "reference-section forming apparatus".

On the other hand, as shown in FIG. 5A, the alteration device 37 includes: a nip-roll mechanism 37n provided in the exterior-sheet contraction unit 30; and a controller 37c which controls the nip-roll mechanism 37n. The nip-roll mechanism 37n includes a pair of upper and lower nip rolls 37nu and 37nd which rotate respectively about rotational axes along CD direction, and the pair of nip rolls 37nu and 37nd are provided in the transport path R30 of the exterior sheet 7a, the transport path R30 being formed between the upstream nip-roll mechanism 31 and the downstream nip-roll mechanism 33 of the exterior-sheet contraction unit 30. The pair of nip rolls 37nu and 37nd are driven and rotated by obtaining driving force from a servo motor (serving as a power source) while the exterior sheet 7a is sandwiched between the outer circumferential surfaces of the nip rolls 37nu and 37nd. Thereby, the exterior sheet 7a is transferred downstream in MD direction.

The sensor 36 includes: an imaging device 36c; and an image processing device 36ip that processes image data transmitted from the imaging device 36c. The imaging device 36c includes, for example, a CCD camera, a processor and a memory. The camera 36cc images the exterior sheet 7a which is being transported between the nip-roll mechanism 37n of the alteration device 37 and the downstream nip-roll mechanism 33 in the transport path R30d (corresponding to the downstream path section).

The imaging is performed according to the foregoing synchronization signal. That is, the imaging device 36c always receives a synchronization signal, and the imaging device 36c performs the imaging when the device 36c detects that the rotational angle value of the synchronization signal matches a predetermined rotational angle value which is stored in the memory of the imaging device 36c in advance. The predetermined rotational angle value is set to such a value that the leg opening 7HL serving as the reference section is positioned within an image indicated with the image data. Every time when the rotational angle value of the synchronization signal matches the predetermined rotational angle value, the imaging device 36c performs the imaging. Accordingly, in this example, the imaging is performed for each leg opening 7HL and its image data is generated. Every time when new image data is generated, the new image data is transmitted to the image processing device 36ip.

The main body of the image processing device 36ip is a suitable computer, and includes a processor and a memory. Every time when image data is transmitted from the imaging device 36c, the image processing device 36ip performs binarization operation as an example of the image processing, according to the transmitted image data. In the binarization operation, concerning a part of the image indicated by the image data in which a leg opening 7HL is imaged, positional coordinates of the pixels of the part is obtained by extracting the pixels of the part. The detail thereof is as follow.

An image indicated by image data consists of a plurality of pixels lined up two dimensionally in X direction and in Y direction. In the image, X direction is CD direction and Y direction is MD direction, for example. The image data has color information corresponding to each pixel. In this example, since image data is a grayscale image, each pixel includes only the brightness as color information. The pixels indicating a leg opening 7HL each have lower brightness than those of the pixels indicating the exterior sheet 7a. And, in the binarization operation, a pixel having a brightness equal to or greater than a certain threshold is assigned to white image, and a pixel having a brightness less than the certain threshold is assigned to black image. This binarization operation makes it possible to extract, as black image, a part of the image in which the leg opening 7HL is imaged. The part in which the leg opening 7HL is imaged is extracted as black image, and the arithmetic average values of the positional coordinates of all pixels constituting the black image can be used as representative positional coordinates, which are representative of the positional coordinates of the pixels of the part in which the leg opening 7HL is imaged.

On the other hand, data of positional coordinates for comparison are stored in advance in the memory of the image processing device 36ip. Here, the positional coordinates for comparison indicate positional coordinates where pixels of the leg opening 7HL should be positioned in the image if the processing units 40, 60 and 70 perform processes according to the synchronization signal precisely at the predetermined target position of the exterior sheet 7a. Of the positional coordinates, the Y coordinate indicates the coordinate in MD direction.

Accordingly, the image processing device 36ip can calculate the shifting amount of the exterior sheet 7a in MD direction based on the difference between the followings: the value of Y coordinate of the comparison positional coordinates; and the value of Y coordinate of the positional coordinates of the pixels of the part in which the leg opening 7HL is imaged, the positional coordinates being obtained by extracting in the binarization operation. Every time when the shifting amount is calculated, the calculated shifting amount is transmitted to the controller 37c of the alteration device 37 in the form of data (corresponding to a detection signal).

The controller 37c controls the alteration device 37 based on the foregoing data. That is, if the data indicates "the exterior sheet 7a is shifted upstream in MD direction", the controller 37c controls an amplifier of each of the servo motors of the nip rolls 37nu and 37nd of the alteration device 37. And, the circumferential speed value of the nip rolls 37nu and 37nd is set to a larger value by a certain alteration amount $\Delta V$ than the current circumferential speed value. The alteration amount $\Delta V$ of the circumferential speed value is calculated, for example, by multiplying the shifting amount by a predetermined gain. The alteration of the circumferential speed value decreases the shifting amount by which the exterior sheet 7a is shift upstream.

On the other hand, if the data indicates "the exterior sheet 7a is shifted downstream in MD direction", the controller 37c controls an amplifier of each of the servo motors of the nip rolls 37nu and 37nd of the alteration device 37. And, the circumferential speed value of the nip rolls 37nu and 37nd is set to a smaller value by a certain alteration amount $\Delta V$ than the current circumferential speed value. Also, in this case, the alteration amount $\Delta V$ of the circumferential speed value is calculated, for example, by multiplying the shifting amount by a predetermined gain. The alteration of the circumferential speed value decreases the shifting amount by which the exterior sheet 7a is shift downstream.

In this example, the alteration is performed every time when the foregoing data is transmitted to the controller 37c. Thus, adjustment for decreasing the shifting amount is made for all of the unit parts of the exterior sheet 7a each of which is to be a diaper 1. However, this invention is not limited thereto. For example, a single alteration may be performed every time when multiple times of data transmissions are made.

In this example, the controller 37c of the alteration device 37 includes an interlock regarding control of the rotations of the nip rolls 37nu and 37nd, and the interlock is in the form of a program or an electric circuit. Accordingly, the circumferential speed values of the nip rolls 37nu and 37nd of the alteration device 37 is altered between an upper limit and a lower limit; the upper limit is the circumferential speed values of the nip rolls 31u and 31d of the upstream nip-roll mechanism 31, and the lower limit is the circumferential speed values of the nip rolls 33u and 33d of the downstream nip-roll mechanism 33. This makes it possible to anticipate and avoid rotation being out of control.

Figure 6:
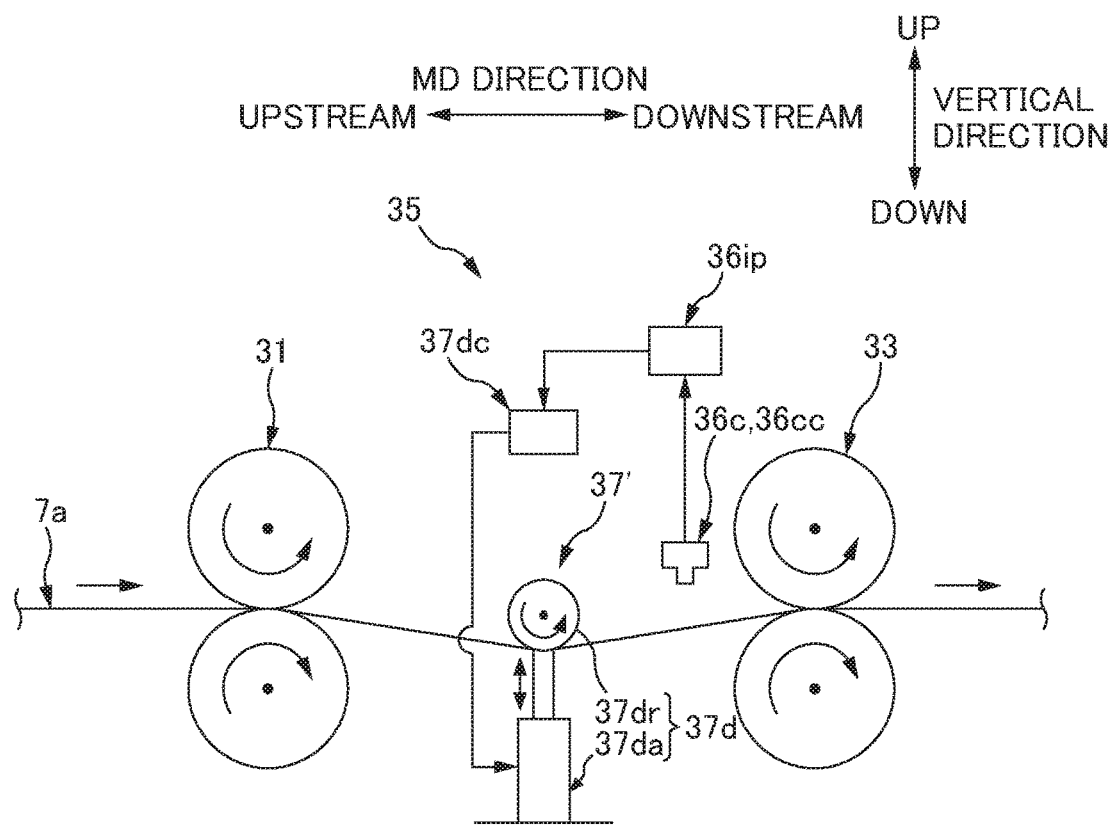
FIG. 6 is a schematic side view of a modified example 37' of an alteration device 37 included in the adjustment device 35.

FIG. 6 is a diagram illustrating a modified example 37' of the alteration device 37. In the foregoing embodiment, the alteration device 37 includes the nip-roll mechanism 37n as shown in FIG. 5A. But, the alteration device 37' in the modified example of FIG. 6 is different in that the alteration device 37' includes a dancer-roll mechanism 37d instead of the nip-roll mechanism 37n. The rest of the configuration is substantially the same as that of the foregoing embodiment. The same components as those of the foregoing embodiment will be denoted by the same reference symbols, and the description thereof is omitted.

As shown in FIG. 6, the dancer-roll mechanism 37d includes: a dancer roll 37dr and an actuator 37da. The dancer roll 37dr is capable of rotating about a rotational axis along CD direction while the exterior sheet 7a being in contact with its outer circumferential surface. The actuator 37da is, for example, a hydraulic cylinder, and the actuator 37da allows the dancer roll 37dr to reciprocate in the thickness direction of the exterior sheet 7a (up-and-down direction) while supporting the dancer roll 37dr in a rotatable manner. To the controller 37dc which controls the actuator 37da, data indicating the foregoing shifting amount is transmitted from the image processing device 36ip.

Then, the controller 37dc controls the alteration device 37' based on the foregoing data. That is, if the data indicates "the exterior sheet 7a is shifted upstream in MD direction", the controller 37dc controls the actuator 37da and moves the dancer roll 37dr upward so that a loop of the exterior sheet 7a becomes smaller. This decreases the shifting amount by which the exterior sheet 7a is shifted upstream. On the other hand, if the data indicates "the exterior sheet 7a is shifted downstream in MD direction, the controller 37dc controls the actuator 37da and moves the dancer roll 37dr downward so that a loop of the exterior sheet 7a becomes larger. This decreases the shifting amount by which the exterior sheet 7a is shifted downstream.

In the foregoing embodiment, as shown in FIG. 4A, the exterior-sheet contraction unit 30 is arranged between the leg-opening forming unit 20 and the absorbent-main-body attaching unit 40. However, the arrangement position is not limited thereto. That is, instead of the foregoing position, the exterior-sheet contraction unit 30 may be arranged between the absorbent-main-body attaching unit 40 and the two-folding unit 50. Or, the unit 30 may be arranged between the two-folding unit 50 and the end-section sealing unit 60, and may be arranged between the end-section sealing unit 60 and the dividing unit 70.

In addition to the area between the leg-opening forming unit 20 and the absorbent-main-body attaching unit 40, an additional exterior-sheet contraction unit 30 may be provided anywhere between the processing units 40, 50, 60 and 70. For example, additional exterior-sheet contraction units 30 may be provided respectively to the following three areas: an area between the absorbent-main-body attaching unit 40 and the two-folding unit 50; an area between the two-folding unit 50 and the end-section sealing unit 60; and an area between the end-section sealing unit 60 and the dividing unit 70. This makes it possible to adjust the exterior sheet 7a to an extended state which is most appropriate to a process by each of the abovementioned four processing units 40, 50, 60 and 70.

In some cases, an additional exterior-sheet contraction unit 30 may be provided to an area which is selected among the foregoing three areas. Or, additional exterior-sheet contraction units 30 may be provided respectively to two areas which are selected among the foregoing three areas.

In the foregoing manufacturing line LM, as shown in FIG. 4A, the absorbent-main-body attaching unit 40 is placed downstream in MD direction from the leg-opening forming unit 20. However, this invention is not limited thereto. For example, as shown in the modified example LM' of the manufacturing line LM illustrated in FIG. 7, the leg-opening forming unit 20 may be arranged downstream in MD direction from the absorbent-main-body attaching unit 40. In this case, however, the leg opening 7HL cannot be used as a reference section which the sensor 36 of the adjustment device 35 detects, and this is because the leg-opening forming unit 20 is located downstream from the adjustment device 35 of the exterior-sheet contraction unit 30. Accordingly, in this case, it is necessary to provide another physical reference section with the exterior sheet 7a. The detail thereof is as follow.

Figure 7:
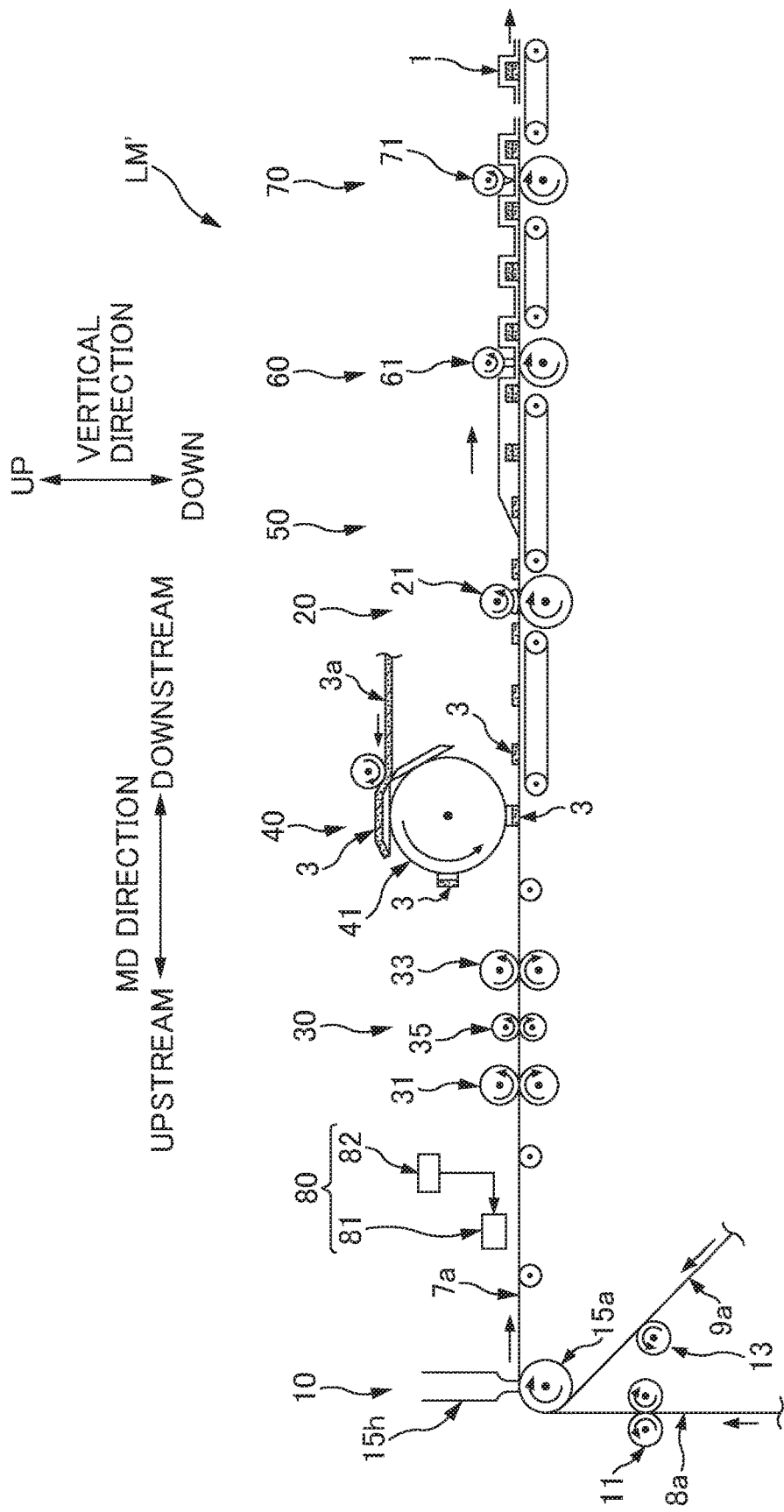
FIG. 7 is a schematic side view of a manufacturing line LM' of a modified example in which a leg-opening forming unit 20 is provided downstream in MD direction from an absorbent-main-body attaching unit 40.

In the example of FIG. 7, a printing unit 80 which prints a mark as a reference section (corresponding to the reference-section forming apparatus) is arranged between the exterior-sheet producing unit 10 and the exterior-sheet contraction unit 30. The printing unit 80 includes a suitable printer 81 and a controller 82 which controls the printer 81. The printer 81 is located in a transport path between the exterior-sheet producing unit 10 and the exterior-sheet contraction unit 30, and prints a mark onto the exterior sheet 7a. Here, the printing is performed according to the foregoing synchronization signal. That is, every time when the rotational angle value of the synchronization signal matches the predetermined rotational angle value, the controller 82 outputs a print instruction signal to the printer 81 so that the printer 81 prints a mark. Thus, the printer 81 prints a mark onto each unit part of the exterior sheet 7a which is to be a diaper 1. Since such a mark is printed according to the synchronization signal as mentioned above, the printing is made with a high accuracy at the predetermined position of the unit part which is to be a diaper 1. Accordingly, the mark can effectively serve as a reference section which indicates a specific position in the exterior sheet 7a.

A type of printer applicable to the printer 81 is not particularly limited as long as the printer can print a mark. For example, an inkjet printer, a flexographic printer, a screen printer and the like are available. A type of the mark is not particularly limited either. For example, the mark may be a pattern, a character, a picture, a symbol or the like.

In the example of FIG. 7, a mark is printed on the stretchable sheet 8a of the exterior sheet 7a. However, this invention is not limited thereto. That is, a mark may be printed on the low-extensible sheet 9a. In this case, the mark can serve as a more accurate reference section. That is, even if an unexpectedly great tension is exerted during transportation after printing, the low-extensible sheet 9a do not greatly deform and can resist the tension due to its low extensibility. This can prevent such a phenomenon as distortion of the mark. Consequently, the mark can effectively serve as an exact reference section.

Other Embodiments

While the embodiment according to the invention are described above, the foregoing embodiment is provided for facilitating the understanding of the invention, and is not to be interpreted as limiting the invention. As a matter of course, the invention can be altered and improved without departing from the gist thereof and the invention includes equivalent thereof. For example, the invention can be altered as described below.

In the foregoing embodiment, a configuration including the imaging device 36c and the image processing device 36ip is provided as an example of the sensor 36 that detects the reference sections. However, this invention is not limited thereto. For example, a configuration including a phototube and a suitable controller may be used as a sensor that detects the reference sections. In this case, the controller can obtain the shifting amount of the exterior sheet 7a in MD direction, based on the difference between the following rotational angle values; one is the rotational angle value of a synchronization signal at the time when the phototube detects passing of the reference section, and the other one is a predetermined rotational angle value which is stored in advance for comparison in a memory of the controller.

In the foregoing embodiment, as shown in FIG. 5A, the sensor 36 that detects the reference sections is configured to detect the leg opening 7HL (serving as the reference section) during the period when the exterior sheet 7a is moving in the transport path R30d (corresponding to the downstream path section) between the nip-roll mechanism 37n of the adjustment device 35 and the downstream nip-roll mechanism 33 of the exterior-sheet contraction unit 30. However, this invention is not limited thereto. For example, the sensor 36 may detect the leg opening 7HL during the period when the exterior sheet 7*a* is moving in the transport path R30*u* (corresponding to the upstream path section) between the upstream nip-roll mechanism 31 of the exterior-sheet contraction unit 30 and the nip-roll mechanism 37*n* of the adjustment device 35. Or, as shown in FIG. 4A, the sensor 36 may detect the leg opening 7HL during the period when the exterior sheet 7*a* is moving in the transport path between the downstream nip-roll mechanism 33 of the exterior-sheet contraction unit 30 and the absorbent-main-body attaching unit 40. That is, the sensor 36 can be used without any problem as long as the sensor 36 is arranged so as to detect the reference section during the time period from the contraction of the exterior sheet 7*a* in the exterior-sheet contraction unit 30 till the attachment of the absorbent main body 3. However, the foregoing configuration does not mean that the sensor 36 is not arranged so as to detect the reference section during the attachment process of the absorbent main body 3 or later. That is, even if the detection is performed during the attachment or later, the sensor 36 can be used without any serious problem. Accordingly, broadly speaking, it is sufficient that the sensor 36 is arranged so as to detect the reference section during the contraction in the exterior-sheet contraction unit 30 or later.

Figure 8:
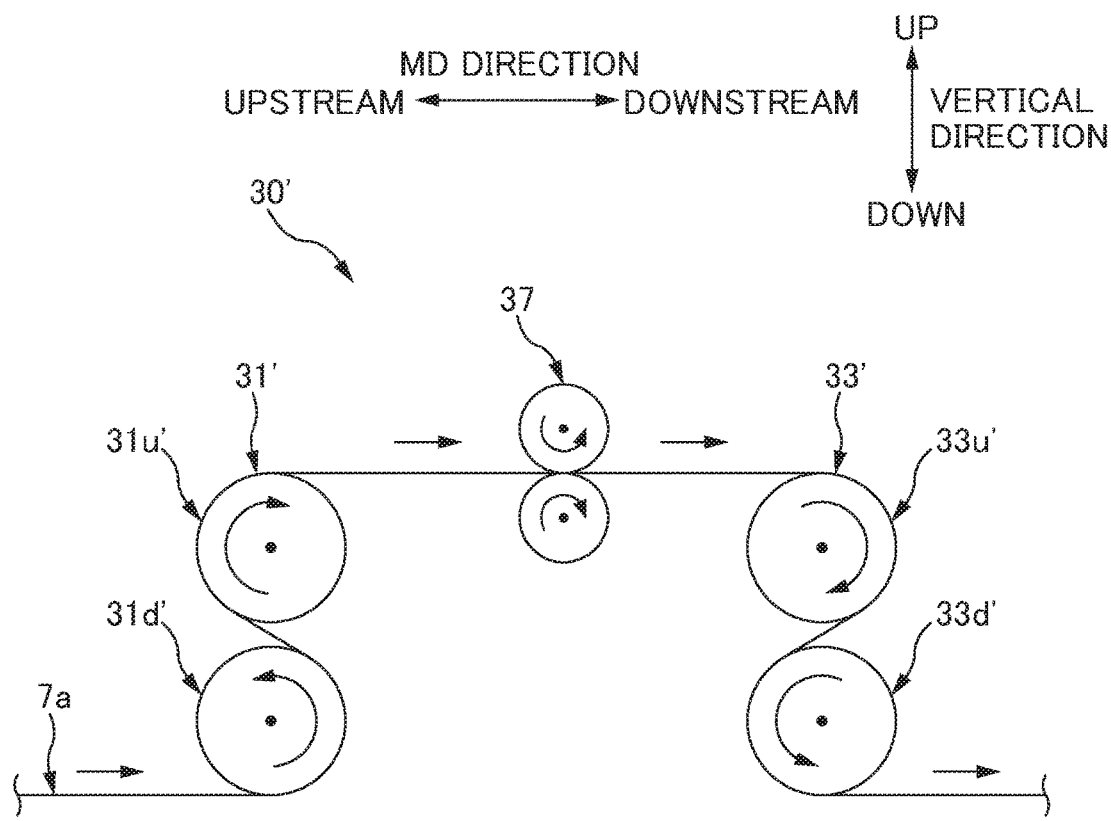
FIG. 8 is a schematic side view of a modified example 30' of an exterior-sheet contraction unit 30.

In the foregoing embodiment, as a mechanism in which the exterior sheet 7*a* in the first extended state contracts, the exterior-sheet contraction unit 30 has a pair of nip-roll mechanisms 31 and 33 as shown in FIG. 5A. However, the invention is not limited thereto as long as a mechanism in which the exterior sheet 7*a* is able to contract. For example, instead of the pair of nip-roll mechanisms 31 and 33, a pair of S-shaped-winding roll mechanisms 31' and 33' shown in FIG. 8 may be provided. That is, each S-shaped-winding roll mechanism 31' (33') includes a pair of rolls 31*u*' and 31*u*' (33*u*' and 33*d*') which are driven and rotated about rotational axes along CD direction while their outer circumferential surfaces facing each other. The exterior sheet 7*a* is wound around the pair of rolls 31*u*' and 31*d*' (33*u*' and 33*d*') in an S shapes. In such a configuration, the outer circumferential surfaces of the rolls 31*u*' and 31*d*' (33*u*' and 33*d*') can hold the exterior sheet 7*a* with substantially no relative sliding. Since these rolls 31*u*' and 31*d*' (33*u*' and 33*d*') are driven and rotated, the exterior sheet 7*a* can be transported at a conveying speed which is equal to the circumferential speed values of the rolls 31*u*' and 31*d*' (33*u*' and 33*d*'). The S-shaped-winding roll mechanisms 31' and 33' can therefore be used instead of the foregoing nip-roll mechanisms 31 and 33. In the example of FIG. 8, both of the nip-roll mechanisms 31 and 33 are replaced with the S-shaped-winding roll mechanisms 31' and 33'. In some cases, either one of the nip-roll mechanisms 31 and 33 may be replaced with the S-shaped-winding roll mechanism 31 (or 33).

Figure 9:
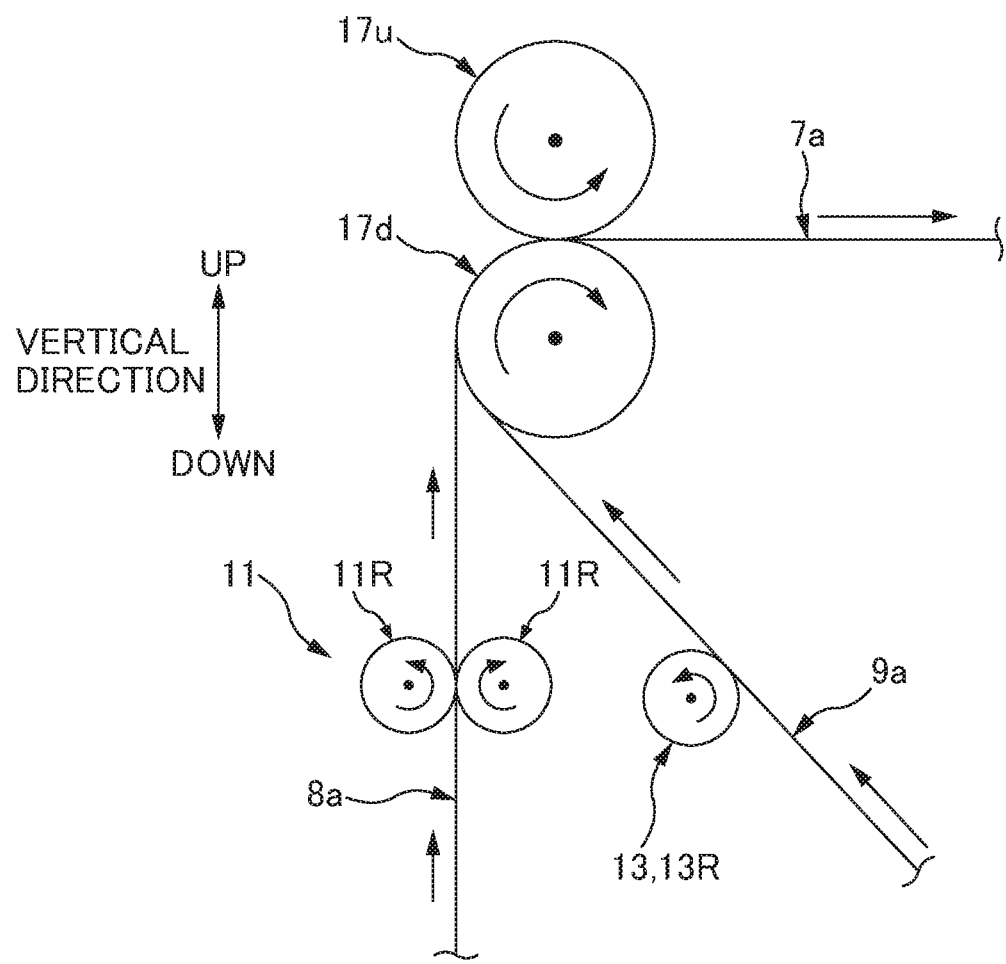
FIG. 9 is a schematic side view of a configuration in which a heat-sealing device or a compression-bonding device is provided instead of an ultrasonic welding device 15 of an exterior-sheet producing unit 10.

In the foregoing embodiment, as shown in FIG. 4A, the stretchable sheet 8*a* and the low-extensible sheet 9*a* are fixed to each other in the exterior-sheet producing unit 10, and the fixing is performed by the ultrasonic welding device 15. However, this invention is not limited thereto. For example, as shown in FIG. 9, instead of the ultrasonic welding device 15, a heat-sealing device or a compression-bonding device may be used. The heat-sealing device and the compression-bonding device have a configuration similar to each other. That is, the main difference between their configurations is whether their rolls are heated or not. Both of the devices include a pair of upper and lower rolls 17*u* and 17*d* which are driven and rotated about rotational axes along CD direction, and each of the rolls 17*u* and 17*d* rotates at the same circumferential speed value as the circumferential speed value V15*a* of the anvil roller 15*a* of the foregoing ultrasonic welding device 15. In such a configuration, the stretchable sheet 8*a* and the low-extensible sheet 9*a* which are stacked passes the nip between the rolls 17*u* and 17*d* while the stretchable sheet 8*a* extending till the reference extended state and the low-extensible sheet 9*a* being extended and tightened. When passing the nip, both sheets 8*a* and 9*a* are pressed by these rolls 17*u* and 17*d* between the rolls. Thus, the sheets 8*a* and 9*a* are be welded or pressed, and are fixed in an integrated manner. In a case of pressing, adhesive such as hot-melt adhesive may be applied, before the pressing, onto at least either one of the stretchable sheet 8*a* and the low-extensible sheet 9*a* in a certain applying pattern.

In the foregoing embodiment, the die cutter device 21 of the leg-opening forming unit 20 includes the single cutter blade 21*c* on the outer circumferential surface of the upper roll 21*u*. However, this invention is not limited thereto. That is, a plurality of the cutter blades 21*c* may be provided on the outer circumferential surface of the upper roll 21*u*. In this case, it is preferable that the plurality of cutter blades 21*c* are arranged at a uniform pitch in the rotating direction of the upper roll 21*u*. It is more preferable that the length of the circular tracks traced by the cutting edge of the cutter blade 21*c* as a result of the rotation of the upper roll 21*u* is an integral multiple of the first pitch P1. In such a configuration, the die-cutting by the cutter blade 21*c* can be stabilized. The same is also true for the heat-sealing device 61 of the end-section sealing unit 60, and is also true for the rotary cutter device 71 of the dividing unit 70. That is, in the foregoing embodiment, the end-section sealing unit 60 also includes the single sealing pattern section 61*sp* in the upper roll 61*u*, and the dividing unit 70 includes the single cutter blade 71*c* in the upper roll 71*u*. However, this invention is not limited thereto. The sealing pattern section 61*sp* which traces a circular track as mentioned above may be provided in the rotating direction at a uniform pitch, and also the cutter blade 71*c* which traces a circular track as mentioned above may be provided in the rotating direction at a uniform pitch.

In the foregoing embodiment, the first extended state, which is an extended state at a time of forming a leg opening 7HL (serving as the reference section), remains in the reference extended state, which is the extended state of the stretchable sheet 8*a* at the time of fixing the stretchable sheet 8*a* and the low-extensible sheet 9*a*. That is, the first extension ratio in the first extended state remains at the extension ratio in the reference extended state. However, this invention is not limited thereto. That is, a leg opening 7HL may be formed at an extension ratio which is slightly smaller than the extension ratio in the reference extended state. In this case, a leg opening 7HL can be formed at the target position in the exterior sheet 7*a* with considerably high accuracy because the extension ratio in the first extended state, which is an extended state at the time of forming a reference section (the leg opening 7HL), is larger than the extension ratio in the second extended state, which is an extended state at the time of processings.

In the foregoing embodiment, in the exterior-sheet producing unit 10, the stretchable sheet 8*a* is fixed to the low-extensible sheet 9*a*. But, a single or a plurality of additional sheet(s) may be fixed together. The additional sheet(s) to be fixed may be a stretchable sheet, or may be a low-extensible sheet. The sheet(s) may be made of nonwoven fabric, woven fabric or film.

REFERENCE SIGNS LIST 1 disposable diaper (absorbent article),
3 absorbent main body, 3e end,
3a continuous body of absorbent main body,
3c absorbent core,
4 top sheet, 4eL projecting part,
5 leak-proof sheet, 5eL projecting part, 5eW projecting part,
7 exterior sheet, 7HL leg opening,
7f ventral part, 7c crotch part, 7b dorsal part, 7eW end,
7a continuous sheet of exterior sheet (exterior sheet, substrate sheet),
8 inner-layer sheet (stretchable sheet),
8a continuous sheet of stretchable sheet (stretchable sheet),
9 outer-layer sheet (low-extensible sheet),
9a continuous sheet of low-extensible sheet (low-extensible sheet),
10 exterior-sheet producing unit (producing device),
11 transport mechanism for stretchable sheet, 11R nip roll,
13 transport mechanism for low-extensible sheet, 13R transport roller,
15 ultrasonic welding device, 15a anvil roller, 15h horn,
17u upper roll, 17d lower roll,
20 leg-opening forming unit (reference-section forming apparatus),
21 die cutter device, 21c cutter blade,
21u cutter roll, 21d anvil roll,
30 exterior-sheet contraction unit (contraction apparatus), 30' exterior-sheet contraction unit (contraction apparatus),
31 upstream nip-roll mechanism, 31u upper nip roll, 31d lower nip roll,
33 downstream nip-roll mechanism, 33u upper nip roll, 33d lower nip roll,
31' S-shaped-winding roll mechanism, 31u' upper roll, 31d' lower roll,
33' S-shaped-winding roll mechanism, 33u' upper roll, 33d' lower roll,
35 adjustment device,
36 sensor, 36c imaging device, 36cc camera, 36ip image processing device,
37 alteration device, 37' alteration device,
37n nip-roll mechanism, 37nu upper nip roll, 37nd lower nip roll,
37c controller,
37d dancer-roll mechanism, 37da actuator, 37dc controller,
37dr dancer roll,
40 absorbent-main-body attaching unit (processing apparatus),
41 rotating-drum device, 42 rotating drum, 43 holding pad, 45 cutter apparatus,
50 two-folded unit,
60 end-section sealing unit (processing apparatus),
61 heat-sealing device, 61u upper roll, 61d lower roll,
61sp sealing pattern section,
70 dividing unit (processing apparatus),
71 rotary cutter device, 71c cutter blade,
71u upper roll (cutter roll), 71d lower roll (anvil roll),
80 printing unit (reference-section forming apparatus), 81 printer,
82 controller,
HB waist opening, HL leg opening,
CV transport mechanism,
S1 first position, S2 second position,
j joined part, jL longitudinal band-like part, jW widthwise band-like part, jC joined part,
LM manufacturing line, LM' manufacturing line,
R30 transport path,
R30u transport path (upstream path section), R30d transport path (downstream path section),
jes sealed end section (joined part),

The invention claimed is:

1. A manufacturing method for manufacturing a composite sheet associated with an absorbent article,
the manufacturing being performed by producing a substrate sheet and performing a certain process to the substrate sheet,
the substrate sheet including a stretchable sheet and a low-extensible sheet,
the low-extensible sheet having an extensibility lower than that of the stretchable sheet,
the manufacturing method comprising:
producing the substrate sheet by fixing the stretchable sheet to at least the low-extensible sheet,
the stretchable sheet continuing along a transporting direction,
the stretchable sheet being transported,
the stretchable sheet being in an extended state in which the stretchable sheet is extended in the transporting direction;
forming a physical reference section on the substrate sheet,
the substrate sheet being in a first extended state and being transported;
causing the substrate sheet to contract until the substrate sheet becomes in a second extended state whose extension ratio is smaller than an extension ratio of the first extended state,
the substrate sheet having the reference section formed on it; and
performing the certain process to the substrate sheet,
the substrate sheet having contracted and being in the second extended state,
causing the substrate sheet to contract including:
transporting the substrate sheet in a transport path;
detecting the reference section by a sensor and outputting a detection signal by a sensor after the contraction; and
altering a transportation state of the substrate sheet in the transport path so that a position in the substrate sheet for the certain process is located close to a target position for the certain process,
the altering being performed according to the detection signal of the sensor.

2. A manufacturing method for manufacturing a composite sheet associated with an absorbent article according to claim 1, wherein the step of altering a transportation state of the substrate sheet in the transport path comprises:
providing an alteration device that includes a roll whose outer circumferential surface comes into contact with the substrate sheet and that is driven and rotated, and
altering the transportation state of the substrate sheet in the transport path by altering a circumferential speed value of the roll.

3. A manufacturing method for manufacturing a composite sheet associated with an absorbent article according to claim 2, wherein:
the alteration device includes a controller that controls the roll according to the detection signal,
when the detection signal indicates that a target position in a substrate sheet for the certain process is shifted upstream in the transporting direction from a position at which the certain process has been performed by the processing apparatus, the controller increases the circumferential speed value of the roll, and when the detection signal indicates that the target position in the substrate sheet for the certain process is shifted downstream in the transporting direction from a position at which the certain process has been performed by the processing apparatus, the controller decreases the circumferential speed value of the roll.

4. A manufacturing method for manufacturing a composite sheet associated with an absorbent article according to claim 1, wherein the step of altering a transportation state of the substrate sheet in the transport path comprises:

providing an alteration device includes a roll whose outer circumferential surface comes into contact with the substrate sheet and that is capable of rotating, and altering the transportation state of the substrate sheet in the transport path by reciprocating motion of the roll along a thickness direction of the substrate sheet.

5. A manufacturing method for manufacturing a composite sheet associated with an absorbent article according to claim 3, wherein:

when the detection signal indicates that a target position in a substrate sheet for the certain process is shifted upstream in the transporting direction from a position at which the certain process has been performed by the processing apparatus, the controller moves the roll in the thickness direction so that a loop of the substrate sheet formed by the roll becomes smaller, and when the detection signal indicates that the target position in the substrate sheet for the certain process is shifted downstream in the transporting direction from a position at which the certain process has been performed by the processing apparatus, the controller moves the roll in the thickness direction so that a loop of the substrate sheet formed by the roll becomes larger.

6. A manufacturing method for manufacturing a composite sheet associated with an absorbent article according to claim 1, wherein:

the reference section comprises a leg opening of the absorbent article that is formed on the substrate sheet, the leg opening being aligned at the first pitch and serving as the reference section.

7. A manufacturing method for manufacturing a composite sheet associated with an absorbent article according to claim 1, wherein:

the reference section comprises a mark that is printed on the substrate sheet as the reference section.

8. A manufacturing method for manufacturing a composite sheet associated with an absorbent article according to claim 6, wherein:

the reference section further comprises a mark that is printed on the substrate sheet as the reference section.

9. A manufacturing method for manufacturing a composite sheet associated with an absorbent article according to claim 7, wherein:

the reference section mark is printed on the low-extensible sheet of the substrate sheet.

10. A manufacturing method for manufacturing a composite sheet associated with an absorbent article according to claim 1, wherein:

on the substrate sheet which is in the first extended state, parts each of which is to be the absorbent article are aligned in the transporting direction at a first pitch, and when a pitch obtained by reducing the first pitch at a ratio of the extension ratio in the second extended state to the extension ratio of the first extended state is defined as a second pitch, the processing apparatus performs the certain process to the substrate sheet at the second pitch.

11. A manufacturing method for manufacturing a composite sheet associated with an absorbent article according to claim 9, wherein:

the absorbent article includes an absorbent main body that absorbs liquid, and the processing apparatus attaches the absorbent main body to the substrate sheet at the second pitch, the attachment being performed as the certain process.

12. A manufacturing method for manufacturing a composite sheet associated with an absorbent article according to claim 9, wherein:

the substrate sheet that is in the second extended state is configured in a two-folded state in which the substrate sheet is two-folded in a width direction of the substrate sheet, and in the processing apparatus, the substrate sheet is fixed in the two-folded state by forming a joined part on the substrate sheet at the second pitch, the forming of the joined part is performed by the processing apparatus as the certain process.

13. A manufacturing method for manufacturing a composite sheet associated with an absorbent article according to claim 1, wherein:

an extension ratio of the substrate sheet in the first extended state remains at an extension ratio in the extended state at a time of the fixing process in the producing device in which the stretchable sheet is fixed to the low-extensible sheet, the low-extensible sheet when is fixed to the stretchable sheet that is in the extended state is extended and tightened, and the reference section is formed for each part of the substrate sheet, the part is a part that is to be the absorbent article.

14. A manufacturing method for manufacturing a composite sheet associated with an absorbent article according to claim 1, wherein:

during a time period from the contraction in the contraction apparatus till the certain process, the sensor detects the reference section and outputs the detection signal.

15. A manufacturing method for manufacturing a composite sheet associated with an absorbent article according to claim 2, wherein:

on the substrate sheet which is in the first extended state, parts each of which is to be the absorbent article are aligned in the transporting direction at a first pitch, and the physical reference section comprises a leg opening of the absorbent article that is formed on the substrate sheet, the leg opening being aligned at the first pitch and serving as the reference section.

16. A manufacturing method for manufacturing a composite sheet associated with an absorbent article according to claim 3, wherein:

on the substrate sheet which is in the first extended state, parts each of which is to be the absorbent article are aligned in the transporting direction at a first pitch, and the physical reference section comprises a leg opening of the absorbent article that is formed on the substrate sheet, the leg opening being aligned at the first pitch and serving as the reference section.

17. A manufacturing method for manufacturing a composite sheet associated with an absorbent article according to claim 4, wherein:
- on the substrate sheet which is in the first extended state, parts each of which is to be the absorbent article are aligned in the transporting direction at a first pitch, and
- the physical reference section comprises a leg opening of the absorbent article that is formed on the substrate sheet,
- the leg opening being aligned at the first pitch and serving as the reference section.

18. A manufacturing method for manufacturing a composite sheet associated with an absorbent article according to claim 5, wherein:
- on the substrate sheet which is in the first extended state, parts each of which is to be the absorbent article are aligned in the transporting direction at a first pitch, and
- the physical reference section comprises a leg opening of the absorbent article that is formed on the substrate sheet,
- the leg opening being aligned at the first pitch and serving as the reference section.

19. A manufacturing method for manufacturing a composite sheet associated with an absorbent article according to claim 2, wherein:
- the physical reference section comprises a mark that is formed on the substrate sheet as the reference section.

20. A manufacturing method for manufacturing a composite sheet associated with an absorbent article according to claim 9, wherein:
- the substrate sheet that is in the second extended state is configured in a two-folded state in which the substrate sheet is two-folded in a width direction of the substrate sheet, and
- in the processing apparatus produces the absorbent article by cutting the substrate sheet at the second pitch,
- the cutting is performed by the processing apparatus as the certain process.

* * * * *